(12) United States Patent
Marnfeldt et al.

(10) Patent No.: US 10,786,665 B2
(45) Date of Patent: Sep. 29, 2020

(54) BIASING OF A CURRENT GENERATION ARCHITECTURE FOR AN IMPLANTABLE MEDICAL DEVICE

(71) Applicant: Boston Scientific Neuromodulation Corporation, Valencia, CA (US)

(72) Inventors: Goran N. Marnfeldt, Valencia, CA (US); Philip L. Weiss, Sherman Oaks, CA (US); Pujitha Weerakoon, Valencia, CA (US); David M. Wagenbach, Simi Valley, CA (US); Emanuel Feldman, Simi Valley, CA (US); Kiran K. Gururaj, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 396 days.

(21) Appl. No.: 15/695,984

(22) Filed: Sep. 5, 2017

(65) Prior Publication Data

US 2018/0071511 A1    Mar. 15, 2018

Related U.S. Application Data

(60) Provisional application No. 62/393,005, filed on Sep. 10, 2016.

(51) Int. Cl.
*A61N 1/00* (2006.01)
*A61N 1/02* (2006.01)
(Continued)

(52) U.S. Cl.
CPC .............. *A61N 1/025* (2013.01); *A61N 1/05* (2013.01); *A61N 1/36* (2013.01); *A61N 1/36125* (2013.01); *G06F 3/05* (2013.01); *H03M 1/66* (2013.01)

(58) Field of Classification Search
CPC . A61N 1/025; A61N 1/05; A61N 1/36; A61N 1/36125; G06F 3/05; H03M 1/66
(Continued)

(56) References Cited

U.S. PATENT DOCUMENTS 5,649,965 A * 7/1997 Pons .................... A61N 1/3706
607/2
5,699,015 A * 12/1997 Dotson ................. H03F 3/3001
330/255

(Continued)

OTHER PUBLICATIONS

International Search Report and Written Opinion regarding corresponding PCT Application No. PCT/US2017/050296, dated Jan. 8, 2018.

*Primary Examiner* — Carl H Layno
*Assistant Examiner* — Michael J Lau
(74) *Attorney, Agent, or Firm* — Lewis & Reese, PLLC

(57) ABSTRACT

Digital-to-analog converter (DAC) circuitry for providing currents at electrodes of an Implantable Pulse Generator (IPG) is disclosed. The DAC circuitry includes at least one PDAC for sourcing current to the electrodes, and at least one NDAC for sinking current from the electrodes. The PDACs are powered with power supplies VH (the compliance voltage) and Vssh in a high power domain, and the NDACs are powered with power supplies Vcc and ground in a low power domain. VH may change during IPG operation, and Vssh preferably also changes with a fixed difference with respect to VH. Digital control signals to the PDACs are formed (and possibly converted into) the high power domain, and transistors used to build the PDACs are biased in the high power domain, and thus may also change with VH. This permits transistors in the PDACs and NDACs to be made from normal low-voltage logic transistors.

22 Claims, 23 Drawing Sheets

(51) Int. Cl.
*A61N 1/36* (2006.01)
*A61N 1/05* (2006.01)
*G06F 3/05* (2006.01)
*H03M 1/66* (2006.01)

(58) Field of Classification Search
USPC .......................................................... 607/72
See application file for complete search history.

(56) References Cited

U.S. PATENT DOCUMENTS

| | | | |
|---|---|---|---|
| 5,804,957 A * | 9/1998 | Coln | A61N 1/0432 323/282 |
| 5,910,156 A * | 6/1999 | Cinbis | A61N 1/3704 607/27 |
| 6,181,969 B1 * | 1/2001 | Gord | A61N 1/08 607/57 |
| 6,516,227 B1 | 2/2003 | Meadows et al. | |
| 6,553,263 B1 | 4/2003 | Meadows et al. | |
| 6,622,048 B1 * | 9/2003 | Mann | A61N 1/36071 607/46 |
| 7,127,298 B1 | 10/2006 | He et al. | |
| 7,177,698 B2 | 2/2007 | Klosterman et al. | |
| 7,180,760 B2 * | 2/2007 | Varrichio | A61N 1/36125 363/59 |
| 7,444,181 B2 | 10/2008 | Shi et al. | |
| 7,539,538 B2 | 5/2009 | Parramon et al. | |
| 7,623,916 B2 | 11/2009 | Julian | |
| 7,801,600 B1 | 9/2010 | Carbunaru et al. | |
| 7,801,602 B2 | 9/2010 | McClure et al. | |
| 7,872,884 B2 | 1/2011 | Parramon et al. | |
| 7,881,803 B2 | 2/2011 | Parramon et al. | |
| 7,890,182 B2 | 2/2011 | Parramon et al. | |
| 8,583,111 B2 * | 11/2013 | Burgener | H03K 19/0944 455/433 |
| 8,606,362 B2 | 12/2013 | He et al. | |
| 8,620,436 B2 | 12/2013 | Parramon et al. | |
| 8,649,858 B2 | 2/2014 | Griffith et al. | |
| 8,768,453 B2 | 7/2014 | Parramon et al. | |
| 9,002,465 B2 | 4/2015 | Ranu | |
| 9,008,790 B2 | 4/2015 | Griffith et al. | |
| 9,037,241 B2 | 5/2015 | Lamont et al. | |
| 9,061,140 B2 | 6/2015 | Shi et al. | |
| 9,155,891 B2 | 10/2015 | Archer | |
| 9,174,051 B2 | 11/2015 | Marnfeldt et al. | |
| 9,220,901 B2 | 12/2015 | Gururaj et al. | |
| 9,233,254 B2 | 1/2016 | Nimmagadda et al. | |
| 9,259,574 B2 | 2/2016 | Aghassian et al. | |
| 9,308,373 B2 | 4/2016 | Lee | |
| 9,314,632 B2 | 4/2016 | Marnfeldt et al. | |
| 9,327,135 B2 | 5/2016 | Vansickle et al. | |
| 9,352,162 B2 | 5/2016 | Lamont et al. | |
| 9,397,639 B2 | 7/2016 | Feldman et al. | |
| 2006/0173493 A1 | 8/2006 | Armstrong et al. | |
| 2007/0038250 A1 * | 2/2007 | He | A61N 1/0551 607/2 |
| 2007/0135868 A1 * | 6/2007 | Shi | A61N 1/36125 607/62 |
| 2007/0156203 A1 * | 7/2007 | Varrichio | H02M 3/07 607/59 |
| 2010/0268309 A1 * | 10/2010 | Parramon | A61N 1/3686 607/116 |
| 2011/0034964 A1 * | 2/2011 | Bi | A61N 1/025 607/5 |
| 2011/0054583 A1 * | 3/2011 | Litt | A61B 5/0478 607/116 |
| 2012/0095529 A1 | 4/2012 | Parramon et al. | |
| 2012/0191146 A1 * | 7/2012 | Markey | A61N 1/372 607/2 |
| 2013/0131771 A1 * | 5/2013 | Lehmann | A61N 1/36038 607/137 |
| 2013/0155763 A1 * | 6/2013 | Alam | G11C 11/1653 365/158 |
| 2013/0184794 A1 * | 7/2013 | Feldman | A61N 1/0534 607/116 |
| 2013/0310897 A1 * | 11/2013 | Marnfeldt | A61N 1/36146 607/62 |
| 2014/0046416 A1 * | 2/2014 | Bennett | A61N 1/0502 607/116 |
| 2015/0134029 A1 | 5/2015 | Ozawa et al. | |
| 2015/0144183 A1 | 5/2015 | Yang et al. | |
| 2015/0157861 A1 | 6/2015 | Aghassian | |
| 2015/0226615 A1 * | 8/2015 | Feldman | A61N 1/3706 374/185 |
| 2016/0008602 A1 * | 1/2016 | Perryman | A61N 1/36125 607/61 |
| 2016/0019964 A1 * | 1/2016 | Sadd | G11C 14/0063 365/185.08 |
| 2016/0038739 A1 * | 2/2016 | Liu | A61N 1/37223 607/45 |
| 2016/0051825 A1 | 2/2016 | Ter-Petrosyan et al. | |
| 2016/0094225 A1 * | 3/2016 | Lim | H03K 5/02 345/174 |
| 2016/0144184 A1 * | 5/2016 | Marnfeldt | A61N 1/36146 607/63 |

\* cited by examiner

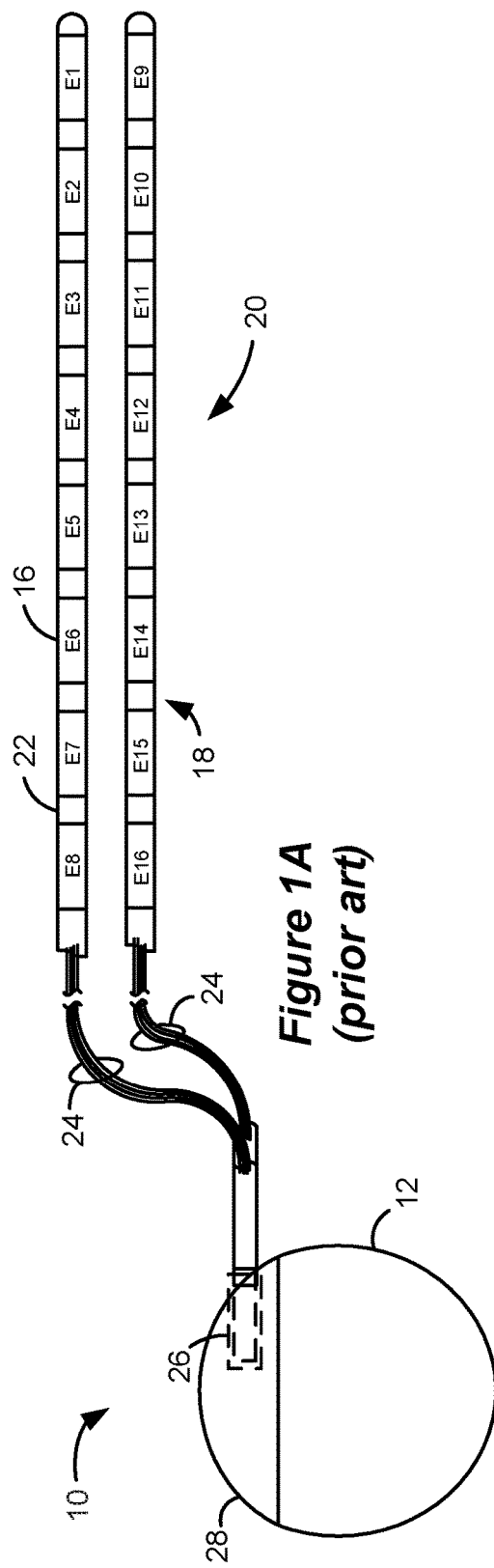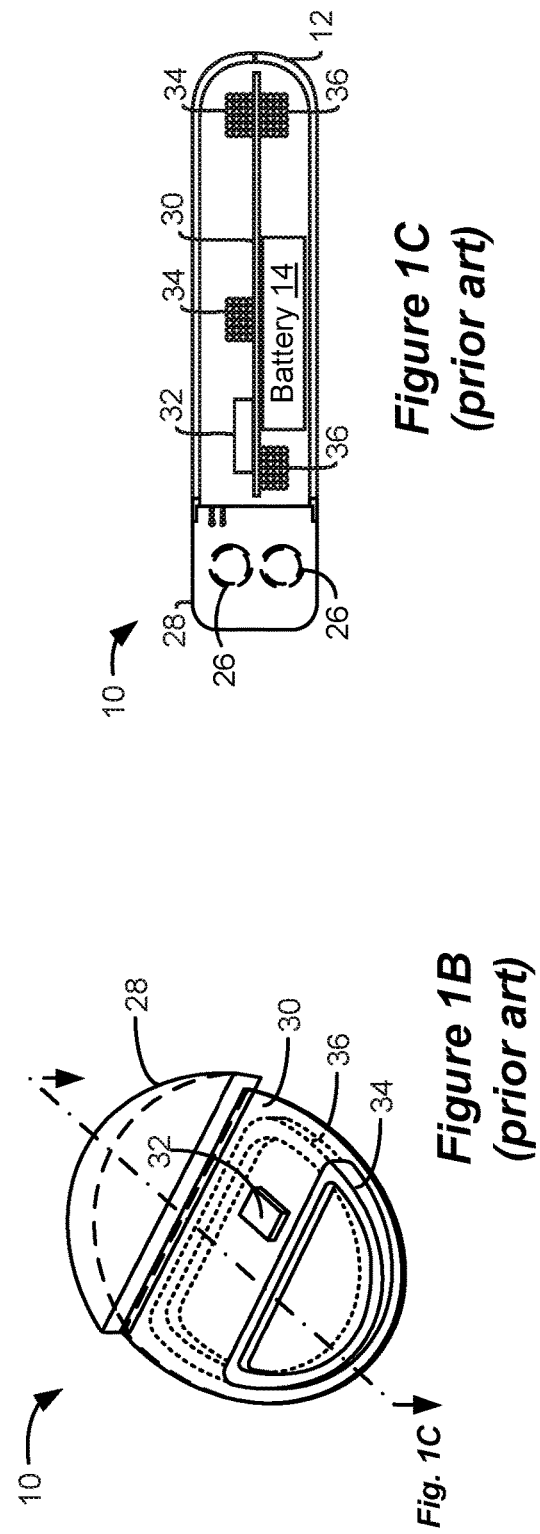
Figure 1A (prior art)
Figure 1B (prior art)
Figure 1C (prior art)

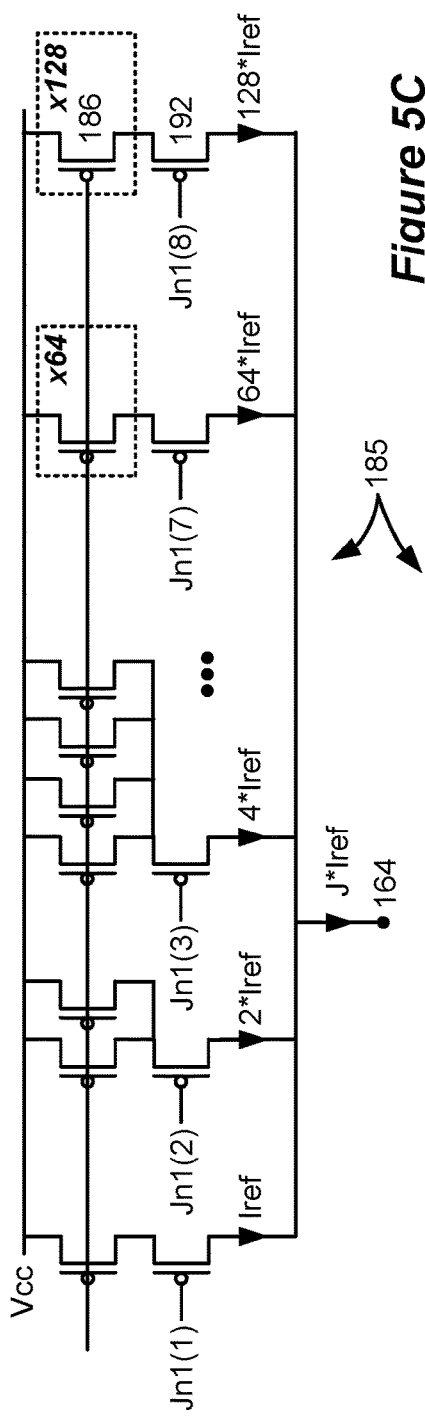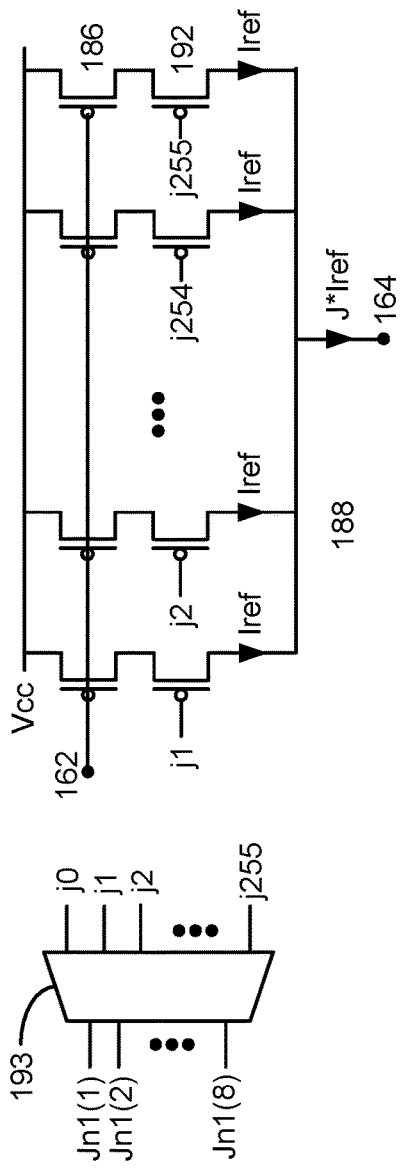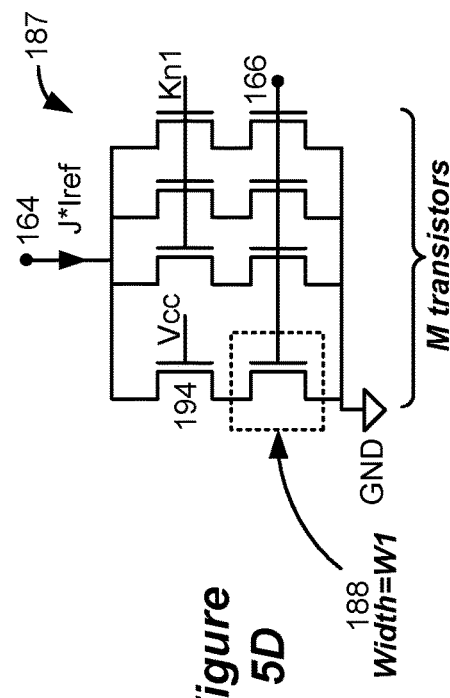
Figure 5C
Figure 5D

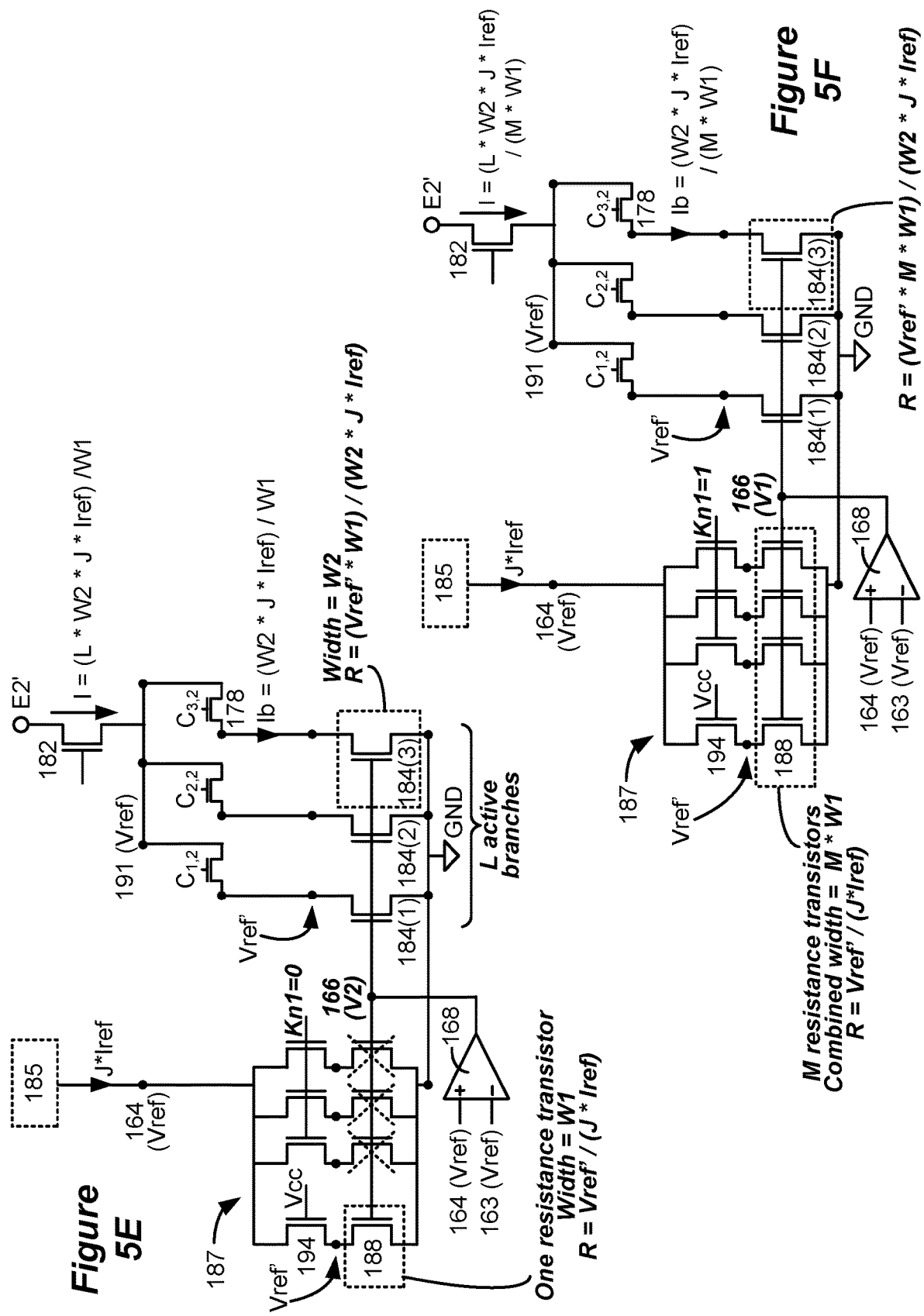

K2 = '0'  
<J2> → J = 100

PDAC2:  
<Cp2> = $C_{1,1}$ to $C_{1,25}$ asserted

NDAC2:

| | <Cn2> | E2 | <Cn2> | E3 |
|---|---|---|---|---|
| t=0 | $C_{2,1}$ to $C_{2,25}$ asserted | -10 mA | $C_{3,1}$ to $C_{3,25}$ deasserted | 0 mA |
| t=1 | $C_{2,1}$ to $C_{2,24}$ asserted | -9.6 mA | $C_{3,25}$ asserted | -0.4 mA |
| t=2 | $C_{2,1}$ to $C_{2,23}$ asserted | -9.2 mA | $C_{3,24}$ to $C_{3,25}$ asserted | -0.8 mA |
| t=3 | $C_{2,1}$ to $C_{2,22}$ asserted | -8.8 mA | $C_{3,23}$ to $C_{3,25}$ asserted | -1.2 mA |
| t=4 | $C_{2,1}$ to $C_{2,21}$ asserted | -8.4 mA | $C_{3,22}$ to $C_{3,25}$ asserted | -1.6 mA |
| ... | | | | |
| t=22 | $C_{2,1}$ to $C_{2,3}$ asserted | -1.2 mA | $C_{3,4}$ to $C_{3,25}$ asserted | -8.8 mA |
| t=23 | $C_{2,1}$ to $C_{2,2}$ asserted | -0.8 mA | $C_{3,3}$ to $C_{3,25}$ asserted | -9.2 mA |
| t=24 | $C_{2,1}$ asserted | -0.4 mA | $C_{3,2}$ to $C_{3,25}$ asserted | -9.6 mA |
| t=25 | $C_{2,1}$ to $C_{2,25}$ deasserted | 0 mA | $C_{3,1}$ to $C_{3,25}$ asserted | -10 mA |

*Figure 9B*

$X = \text{'1'}$
$K = \text{'1'}$
$\langle J \rangle \rightarrow J = 100$

PDAC:
$\langle Cp1 \rangle$ to $\langle Cp4 \rangle = C_{1,1}$ to $C_{1,100}$ asserted

| NDAC: | $\langle Cn1 \rangle$ to $\langle Cn4 \rangle$ | E2 | $\langle Cn1 \rangle$ to $\langle Cn4 \rangle$ | E3 |
|---|---|---|---|---|
| t=0 | $C_{2,1}$ to $C_{2,100}$ asserted | -10 mA | $C_{3,1}$ to $C_{3,100}$ deasserted | 0 mA |
| t=1 | $C_{2,1}$ to $C_{2,99}$ asserted | -9.9 mA | $C_{3,100}$ asserted | -0.1 mA |
| t=2 | $C_{2,1}$ to $C_{2,98}$ asserted | -9.8 mA | $C_{3,99}$ to $C_{3,100}$ asserted | -0.2 mA |
| t=3 | $C_{2,1}$ to $C_{2,97}$ asserted | -9.7 mA | $C_{3,98}$ to $C_{3,100}$ asserted | -0.3 mA |
| t=4 | $C_{2,1}$ to $C_{2,96}$ asserted | -9.6 mA | $C_{3,97}$ to $C_{3,100}$ asserted | -0.4 mA |
| ... | ... | ... | ... | ... |
| t=97 | $C_{2,1}$ to $C_{2,3}$ asserted | -0.3 mA | $C_{3,4}$ to $C_{3,100}$ asserted | -9.7 mA |
| t=98 | $C_{2,1}$ to $C_{2,2}$ asserted | -0.2 mA | $C_{3,3}$ to $C_{3,100}$ asserted | -9.8 mA |
| t=99 | $C_{2,1}$ asserted | -0.1 mA | $C_{3,2}$ to $C_{3,100}$ asserted | -9.9 mA |
| t=100 | $C_{2,1}$ to $C_{2,100}$ deasserted | 0 mA | $C_{3,1}$ to $C_{3,100}$ asserted | -10 mA |

*Figure 10C*

| <X> | mode | Kx | Ky | PDACs/NDACs combined | # timing channels | Imax (@Jmax, Lmax) in each timing channel | Lmax (number of branches) in each timing channel | resolution |
|---|---|---|---|---|---|---|---|---|
| 00 | standard | 0 | 0 | none | 4 | +/- 25.5 mA | 25 | 4% |
| 01 | medium | 1 | 0 | PDACs 1-2; PDACs 3-4/ NDACs 1-2; NDACs 3-4 | 2 | +/- 25.5 mA | 50 | 2% |
| 10 | high | 1 | 1 | PDACs 1-4 / NDACs 1-4 | 1 | +/- 25.5 mA | 100 | 1% |

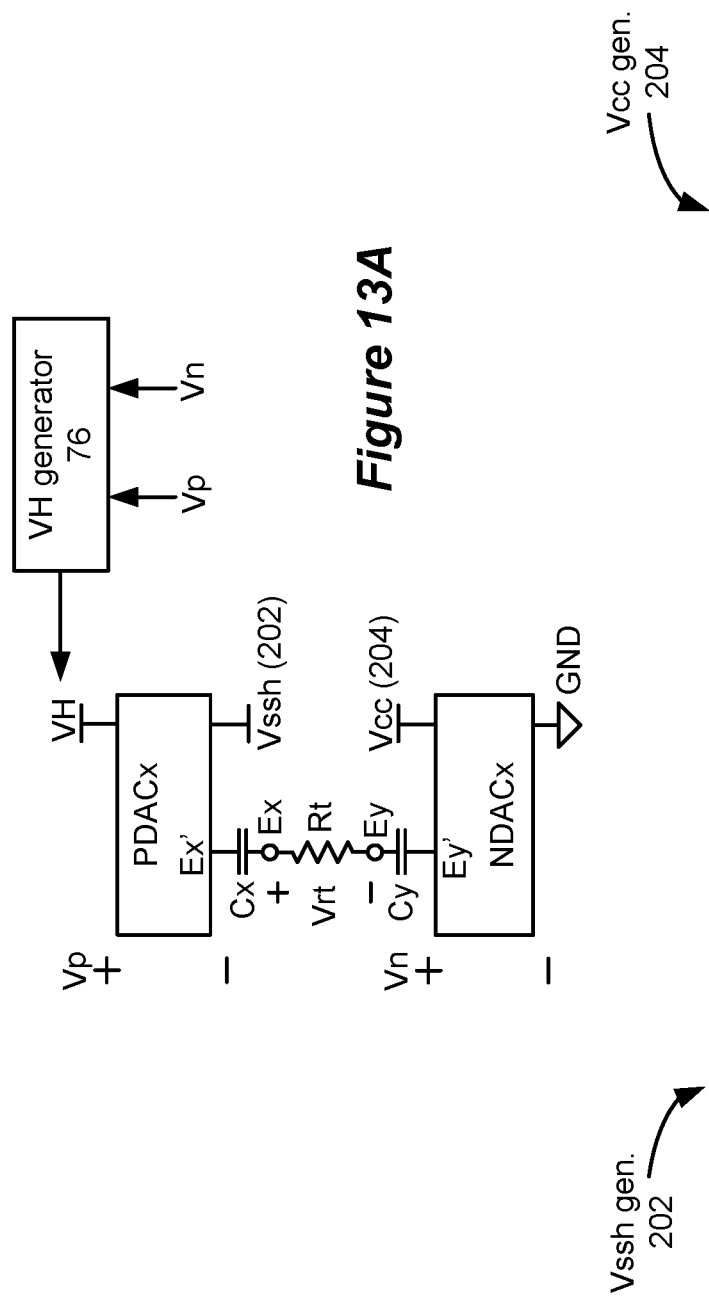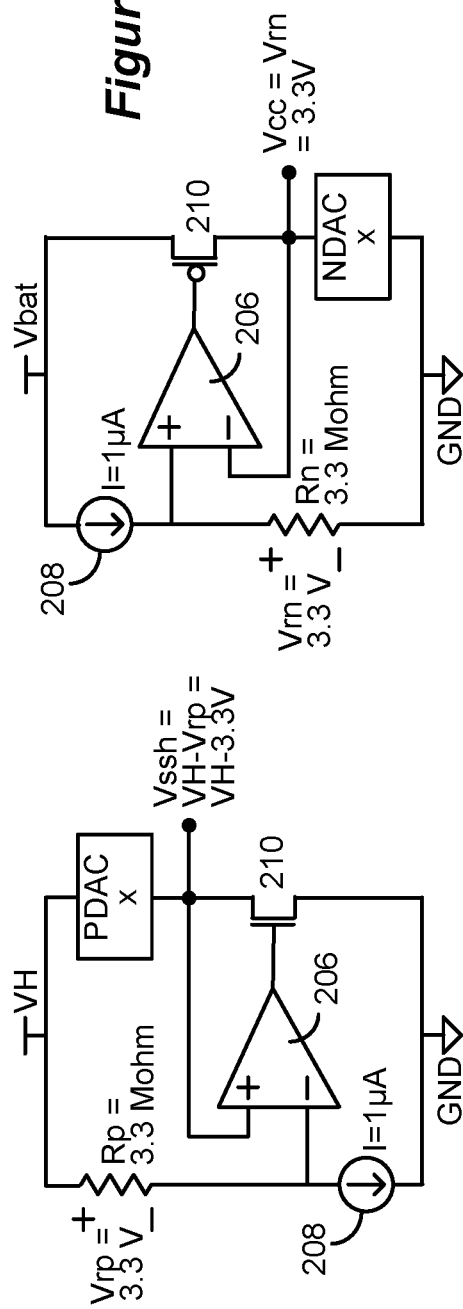
Figure 13A
Figure 13B

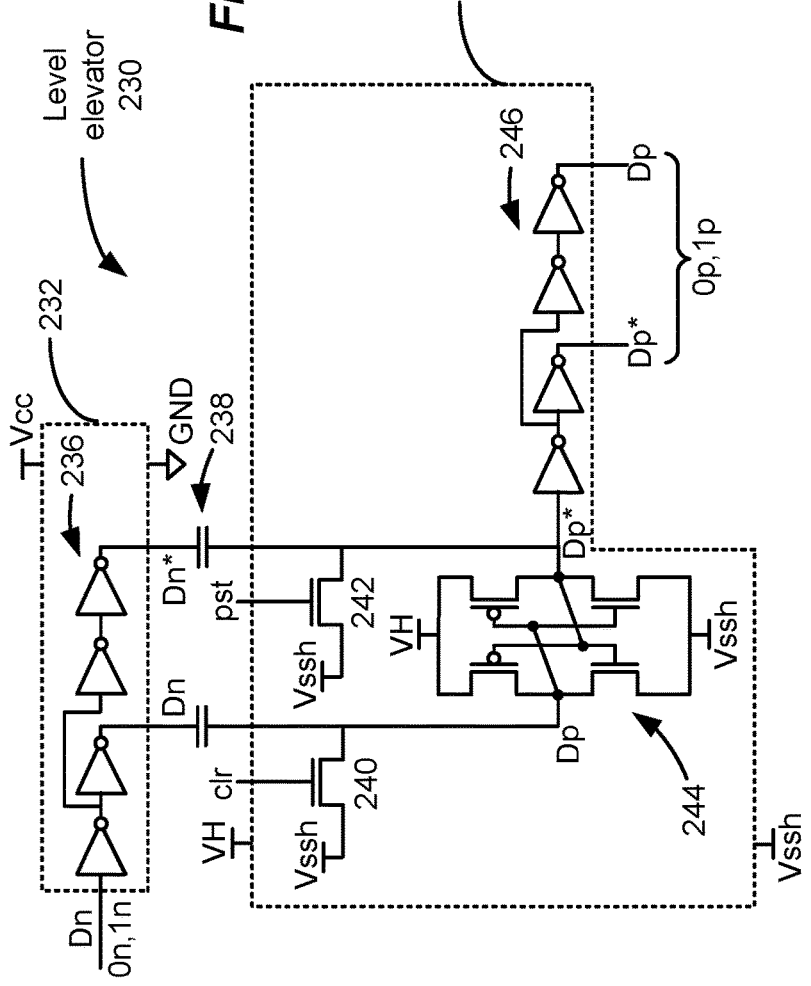
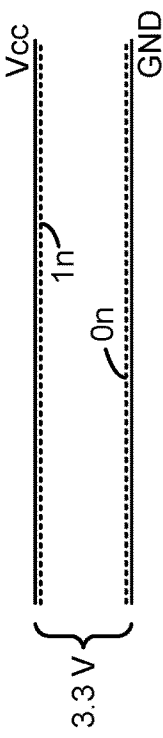
*Figure 14C*
*Figure 14D*

BIASING OF A CURRENT GENERATION ARCHITECTURE FOR AN IMPLANTABLE MEDICAL DEVICE

CROSS REFERENCE TO RELATED APPLICATIONS

This is a non-provisional application of U.S. Provisional Patent Application Ser. No. 62/393,005, filed Sep. 10, 2016, which is incorporated by reference in its entirety, and to which priority is claimed.

FIELD OF THE INVENTION

The present invention relates generally to implantable medical devices, and more particularly to improved current generation architectures for an implantable pulse generator.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, an SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the circuitry and power source (e.g., battery) 14 (FIG. 1C) necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on two leads 18 for a total of sixteen electrodes 16, although the number of leads and electrodes is application specific and therefore can vary. The leads 18 couple to the IPG 10 using lead connectors 26, which are fixed in a non-conductive header material 28, which can comprise an epoxy for example.

As shown in the cross-section of FIG. 1C, the IPG 10 typically includes a printed circuit board (PCB) 30, along with various electronic components 32 mounted to the PCB 30, some of which are discussed subsequently. Two coils (more generally, antennas) are shown in the IPG 10: a telemetry coil 34 used to transmit/receive data to/from an external controller (not shown); and a charging coil 36 for charging or recharging the IPG's battery 14 using an external charger (not shown). FIG. 1B shows these aspects in perspective with the case 12 removed for easier viewing. Telemetry coil 34 may alternatively comprise a short range RF antenna for wirelessly communicating in accordance with a short-range RF standard such as Bluetooth, WiFi, MICS, Zigbee, etc., as described in U.S. Patent Application Publication 2016/0051825.

FIG. 2A shows a prior art architecture 40 for the circuitry in IPG 10, which is disclosed in U.S. Patent Application Publications 2012/0095529, 2012/0092031 and 2012/0095519 ("ASIC Publications"), which are incorporated by reference in their entireties. Architecture 40 includes a microcontroller integrated circuit 50 and an Application Specific Integrated Circuit (ASIC) 60 in communication with each other by a bus 90. Stated simply, the microcontroller 50 provides master control for the architecture 40, while ASIC 60 takes commands from and provides data to the microcontroller. ASIC 60 provides specific IPG functionality. For example, and as explained in further detail below, ASIC 60 send stimulation current to and reads measurements from the sixteen electrodes 16. ASIC 60 comprises a mixed mode IC carrying and processing both analog and digital signals, whereas microcontroller 50 comprises a digital IC carrying and processing only digital signals.

Microcontroller 50 and ASIC 60 comprise monolithic integrated circuits each formed on their own semiconductive substrates ("chips"), and each may be contained in its own package and mounted to the IPG 10's PCB 30. Architecture 40 may also include additional memory (not shown) for storage of programs or data beyond that provided internally in the microcontroller 50. Additional memory may be connected to the microcontroller 50 by a serial interface (SI) as shown, but could also communicate with the microcontroller 50 via bus 90. Bus 90 may comprise a parallel address/data bus, and may include a clock signal and various control signals to dictate reading and writing to various memory locations, as explained in the '529 Publication. Bus 90 and the signals it carries may also take different forms; for example, bus 90 may include separate address and data lines, may be serial in nature, etc.

As explained in the above-referenced ASIC Publications, architecture 40 is expandable to support use of a greater number of electrodes 16 in the IPG 10. For example, and as shown in dotted lines in FIG. 2A, architecture 40 may include another ASIC 60' identical in construction to ASIC 60, thus expanding the number of electrodes supported by the IPG 10 from sixteen to thirty two. Various off-bus connections 54 (i.e., connections not comprising part of bus 90) can facilitate such expansion, and may further (e.g., by bond programming; see inputs M/S) designate ASIC 60 as a master and ASIC 60' as a slave. Such differentiation between the ASICs 60 and 60' can be useful, as certain redundant functionality in the slave ASIC 60' can be disabled in favor of the master ASIC 60. Off-bus communications 54 can allow the voltage at the electrodes nodes 61a (E1'-E16') of one of the ASICs (60'; OUT1, OUT2) to be sent to the other ASIC (60; IN1, IN2) to be measured. Off-bus connections 54 are further useful in generation and distribution of a clock signal governing communications on the bus 90 as well as in the ASIC(s) 60. As these concepts are discussed in detail in the above-referenced ASIC Publications, they are not elaborated upon here.

FIG. 2B shows various functional circuit blocks within ASIC 60, which are briefly described. ASIC 60 includes an internal bus 92 which can couple to external bus 90 and which may duplicate bus 90's signals. Note that each of the functional blocks includes interface circuitry 88 enabling communication on the internal bus 92 and ultimately external bus 90, as the above-referenced ASIC Publications explain. Interface circuitry 88 includes circuitry to help each block recognize when bus 92 is communicating data with addresses belonging to that block. ASIC 60 contains several terminals 61 (e.g., pins, bond pads, solder bumps, etc.), such as those necessary to connect to the bus 90, the battery 14, the coils 34, 36, external memory (not shown). Terminals 61 include electrode node terminals 61a (E1'-E16') which connect to the electrodes 16 (E1-E16) on the lead(s) 18 by way of DC-blocking capacitors 55. As is known, DC-blocking capacitors 55 are useful to ensure that DC current isn't inadvertently (e.g., in the event of failure of the ASIC 60's circuitry) injected into the patient's tissue, and hence provide safety to the IPG 10. Such DC-blocking capacitors 55 can be located on or in the IPG 10's PCB 30 (FIG. 1C) inside of the IPG's case 12. See U.S. Patent Application Publication 2015/0157861.

Each of the circuit blocks in ASIC 60 performs various functions in IPG 10. Telemetry block 64 couples to the IPG telemetry coil 34, and includes transceiver circuitry for wirelessly communicating with an external device according to a telemetry protocol. Such protocol may comprise Frequency Shift Keying (FSK), Amplitude Shift Keying (ASK), or various short-range RF standards such as those mentioned above. Charging/protection block 62 couples to the IPG charging coil 38, and contains circuitry for rectifying power wirelessly received from an external charger (not shown), and for charging the battery 14 in a controlled fashion.

Analog-to-Digital (A/D) block 66 digitizes various analog signals for interpretation by the IPG 10, such as the battery voltage Vbat or voltages appearing at the electrodes, and is coupled to an analog bus 67 containing such voltages. A/D block 66 may further receive signals from sample and hold block 68, which as the ASIC Publications explain can be used to measure such voltages, or differences between two voltages. For example, sample and hold circuitry 68 may receive voltages from two electrodes and provide a difference between them (see, e.g., Ve1-Ve2 in FIG. 3, discussed subsequently), which difference voltage may then be digitized at A/D block 66. Knowing the difference in voltage between two electrodes when they pass a constant current allows for a determination of the (tissue) resistance between them, which is useful for a variety of reasons.

Sample and hold block 68 may also be used to determine one or more voltage drops across the DAC circuitry 72 (see Vp and Vn in FIG. 3, explained subsequently) used to create the stimulation pulses. This is useful to setting the compliance voltage VH to be output by a compliance voltage generator block 76. Compliance voltage VH powers the DAC circuitry 72, and the measured voltage drops can be used to ensure that the compliance voltage VH produced is optimal for the stimulation current to be provided—i.e., VH is not too low to be unable to produce the current required for the stimulation, nor too high so as to waste power in the IPG 10. Measuring Vp and Vn to determine whether VH is too high or too low is particularly useful because the resistance Rt of the patient's tissue may not be known in advance, or may change over time. Thus, the voltage drop across the tissue, Vrt, may change as well, and monitoring Vp and Vn provides an indication of such changes, and hence whether VH should be adjusted. Compliance voltage generator block 76 includes circuitry for boosting a power supply voltage such as the battery voltage, Vbat, to a proper level for VH. Such boost circuitry (some of which may be located off chip) can include an inductor-based boost converter or a capacitor-based charge pump, which are described in detail in U.S. Patent Application Publication 2010/0211132.

Clock generation block 74 can be used to generate a clock for the ASIC 60 and communication on the bus. Clock generation block 74 may receive an oscillating signal from an off-chip crystal oscillator 56, or may comprise other forms of clock circuitry located completely on chip, such as a ring oscillator. U.S. Patent Application Publication 2014/0266375 discloses another on-chip circuit that can be used to generate a clock signal on the ASIC 60.

Master/slave control block 86 can be used to inform the ASIC 60 whether it is to be used as a master ASIC or as a slave ASIC (e.g., 60'), which may be bond programmed at M/S terminal 61. For example, M/S terminal may be connected to a power supply voltage (e.g., Vbat) to inform ASIC 60 that it will operate as a master ASIC, or to ground to inform that it will operate as a slave, in which case certain function blacks will be disabled, as the ASIC Publications explain.

Interrupt controller block 80 receives various interrupts (e.g., INT1-INT4) from other circuit blocks, which because of their immediate importance are received independent of the bus 92 and its communication protocol. Interrupts may also be sent to the microcontroller 50 via the bus 90. Internal controller 82 in the ASIC 60 may receive indication of such interrupts, and act a controller for all other circuit blocks, to the extent microcontroller 50 (FIG. 2A) does not handle such interrupt through the external bus 90. Further, each of the functional circuit blocks contain set-up and status registers (not shown) written to by the controller 82 upon initialization to configure and enable each block. Each functional block can then write pertinent data at its status registers, which can in turn be read by the controller 82 via internal bus 92 as necessary, or by the microcontroller 50 via external bus 90. The functional circuit blocks can further simple state machines to manage their operation, which state machines are enabled and modified via each block's set-up and status registers.

Nonvolatile memory (NOVO) block 78 caches any relevant data in the system (such as log data). Additional memory (not shown) can also be provided off-chip via a serial interface block 84.

ASIC 60 further includes a stimulation circuit block 70, which includes circuitry for receiving and storing stimulation parameters from the microcontroller 50 via buses 90 and 92. Stimulation parameters define the shape and timing of stimulation pulses to be formed at the electrodes, and can include parameters such as which electrodes E1-E16 will be active; whether those active electrodes are to act as anodes that source current to a patient's tissue, or cathodes that sink current from the tissue; and the amplitude (A), duration (d), and frequency (f) of the pulses. Amplitude may comprise a voltage or current amplitude. Such stimulation parameters may be stored in registers in the stimulation circuitry block 70. See, e.g., U.S. Patent Application Publications 2013/0289661; 2013/0184794.

Block 70 also includes a Digital-to-Analog Converter (DAC) 72 for receiving the stimulation parameters from the registers and for forming the prescribed pulses at the selected electrodes. FIG. 3 shows a simple example of DAC circuitry 72 as used to provide a current pulse between selected electrodes E1 and E2 and through a patient's tissue, Rt. DAC circuitry 72 as shown comprises two portions, denoted as PDAC 72p and NDAC 72n. These portions of DAC circuitry 72 are so named because of the polarity of the transistors used to build them and the polarity of the current they provide. Thus, PDAC 72p is formed from P-channel transistors and is used to source a current +I to the patient's tissue Rt via a selected electrode E1 operating as an anode.

NDAC 72n is formed of N-channel transistors and is used to sink current −I from the patient's tissue via a selected electrode E2. It is important that current sourced to the tissue at any given time equal that sunk from the tissue to prevent charge from building in the tissue, although more than one anode electrode and more than one cathode electrode may be operable at a given time.

PDAC 72p and NDAC 72n receive digital control signals from the registers in the stimulation circuitry block 70, denoted <Pstim> and <Nstim> respectively, to generate the prescribed pulses with the prescribed timing. In the example shown, PDAC 72p and NDAC 72n comprise current sources, and in particular include current-mirrored transistors for mirroring (amplifying) a reference current Iref to produce pulses with an amplitude (A) of I. PDAC 72p and NDAC 72n could however also comprise constant voltage sources. Control signals <Pstim> and <Nstim> also prescribe the timing of the pulses, including their duration (D) and frequency (f), as shown in the waveforms generated at the selected electrodes. The PDAC 72p and NDAC 72n along with the intervening tissue Rt complete a circuit between a power supply VH—the compliance voltage as already introduced—and ground. As noted earlier, the compliance voltage VH is adjustable to an optimal level at compliance voltage generator block 76 (FIG. 2B) to ensure that current pulses of a prescribed amplitude can be produced without unnecessarily wasting IPG power.

The DAC circuitry 72 (PDAC 72p and NDAC 72n) may be dedicated at each of the electrodes, and thus may be activated only when its associated electrode is to be selected as an anode or cathode. See, e.g., U.S. Pat. No. 6,181,969. Alternatively, one or more DACs (or one or more current sources within a DAC) may be distributed to a selected electrode by a switch matrix (not shown), in which case optional control signals <Psel> and <Nsel> would be used to control the switch matrix and establish the connection between the selected electrode and the PDAC 72p or NDAC 72n. See, e.g., U.S. Pat. No. 8,606,362. DAC circuitry 72 may also use a combination of these dedicated and distributed approaches. See, e.g., U.S. Pat. No. 8,620,436.

In the example waveform shown, the pulses provided at the electrodes are biphasic, meaning that each pulse comprises a first phase 94a of a first polarity, followed by a second phase 94b of an opposite polarity. This is useful as a means of active recovery of charge that may build up on the DC-blocking capacitors 55. Thus, while charge will build up on the capacitors 55 during the first pulse phase 94a, the second pulse phase 94b will actively recover that charge, particularly if the total amount of charge is equal in each phase (i.e., of the area under the first and second pulse phases are equal). Recovery of excess charge on the DC-blocking capacitors 55 is important to ensure that the DAC circuit 72 will operate as intended: if the charge/voltage across the DC-blocking capacitors 55 is not zero at the end of each pulse, remaining charge/voltage will skew formation of subsequent pulses, which may therefore not provide the prescribed amplitude.

While active recovery of charge using a biphasic pulse is beneficial, such active recovery may not be perfect, and hence some residual charge may remain on the DC-blocking capacitors 55 even after the second phase 94b of the biphasic pulse. Thus, the art has recognized the utility of passive charge recovery. Passive charge recovery is implemented with the stimulation circuit block 70, and includes use of passive recovery switches (transistors) 96, which are connected between the electrode nodes (E1'-E16') 61a and a common reference voltage. This voltage as shown may simply comprise the battery voltage, Vbat, but another reference voltage could also be used. Closing the passive recovery switches 96 during a time period 98 after the second pulse phase 94b couples the DC-blocking capacitors 55 in parallel between the reference voltage and the patient's tissue. Given the previous serial connection of the DC-blocking capacitors, this should normalize any remaining charge.

BRIEF DESCRIPTION OF THE DRAWINGS

FIGS. 1A-1C show an Implantable Pulse Generator (IPG), and the manner in which an electrode array is coupled to the IPG, in accordance with the prior art.

FIG. 5C shows the circuitry details of a master DAC within the NDAC of FIG. 5B, in accordance with an example of the invention.

FIG. 5D shows circuitry details of as resistance block within the NDAC of FIG. 5B, in accordance with an example of the invention.

FIGS. 5E and 5F show details regarding the formation of currents in each of the branches in standard and high-resolution current modes respectively, in accordance with examples of the invention.

FIGS. 9A and 9B show use of the improved DAC to move current between cathode electrodes in a timing channel, in accordance with an example of the invention.

FIGS. 10A-10C show operation of the improved DAC circuitry in a high resolution current mode, which combines all PDACs together and combines all NDACs together to form a single timing channel with higher resolution, in accordance with an example of the invention.

FIG. 13A shows the high power domain (VH/Vssh) operable in the PDACs and the low power domain (Vcc/ground) operable in the NDACs, and shows how compliance voltage VH can be varied, in accordance with an example of the invention.

FIG. 13B shows generators used to produce Vssh and Vcc, in accordance with examples of the invention.

FIG. 14C shows example level elevation circuitry for each control signal, in accordance with examples of the invention.

FIG. 14D shows how the high power domain and its logic levels can vary as the compliance voltage changes, in accordance with an example of the invention.

DETAILED DESCRIPTION

Figure 4A:
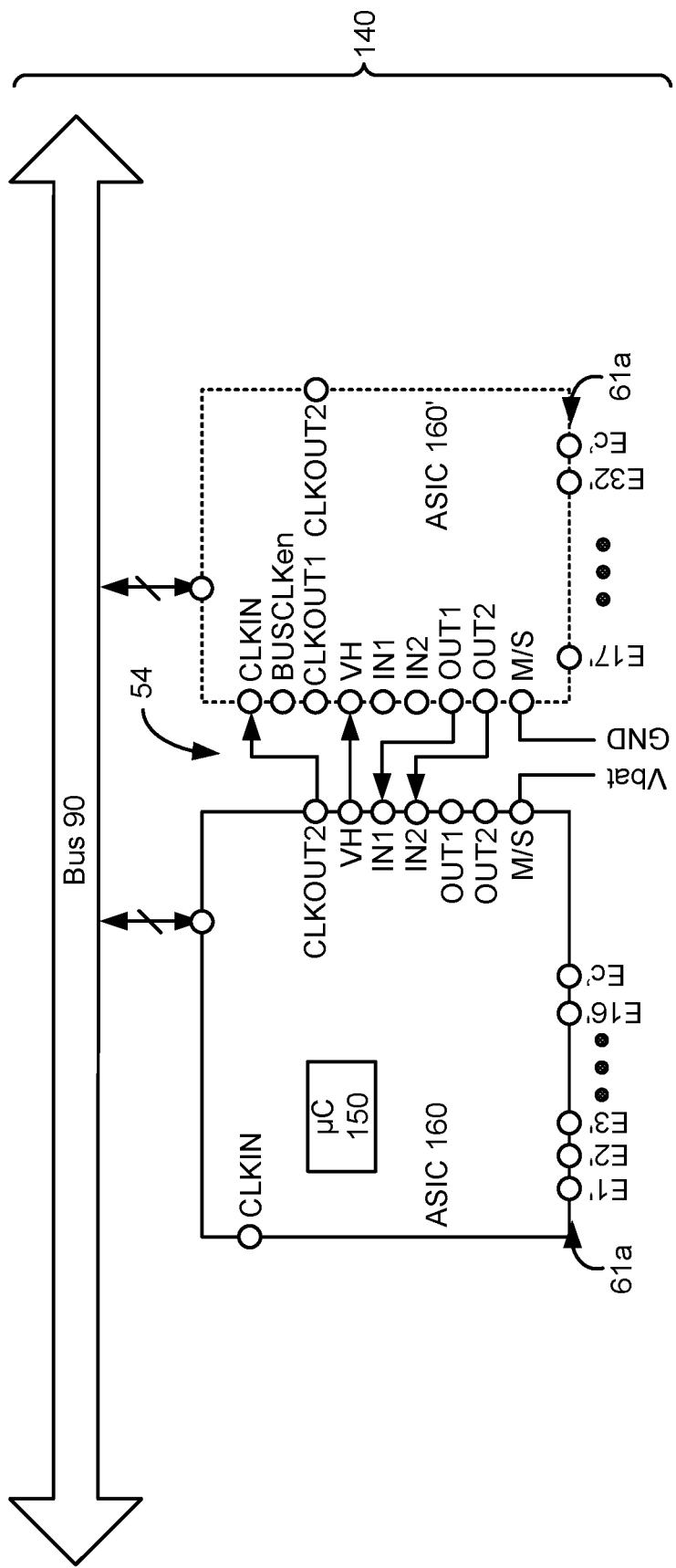
FIG. 4A shows an improved architecture for an IPG, in which an improved ASIC includes a microcontroller, in accordance with an example of the invention.
Figure 4B:
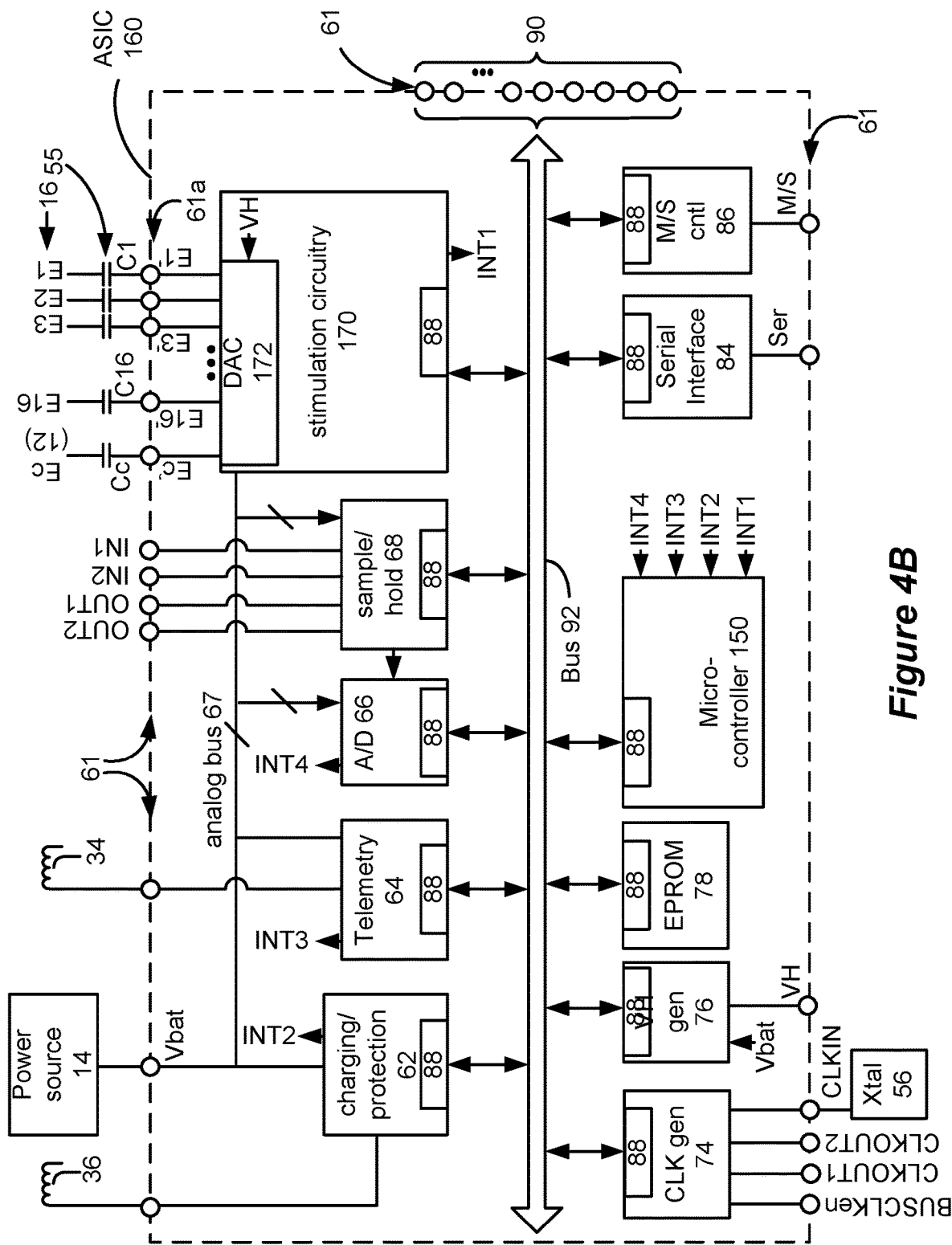
FIG. 4B shows circuitry blocks within the improved ASIC, including improved stimulation circuitry and its improved DAC circuitry, in accordance with an example of the invention.

FIGS. 4A and 4B show an improved architecture 140 and ASIC 160 for an IPG such as IPG 10 described earlier. Elements in architecture 140 and ASIC 160 that can remain unchanged from the prior art architecture 40 and ASIC 60 described in the Background bear the same elements numerals, and are not described again.

Figure 2A:
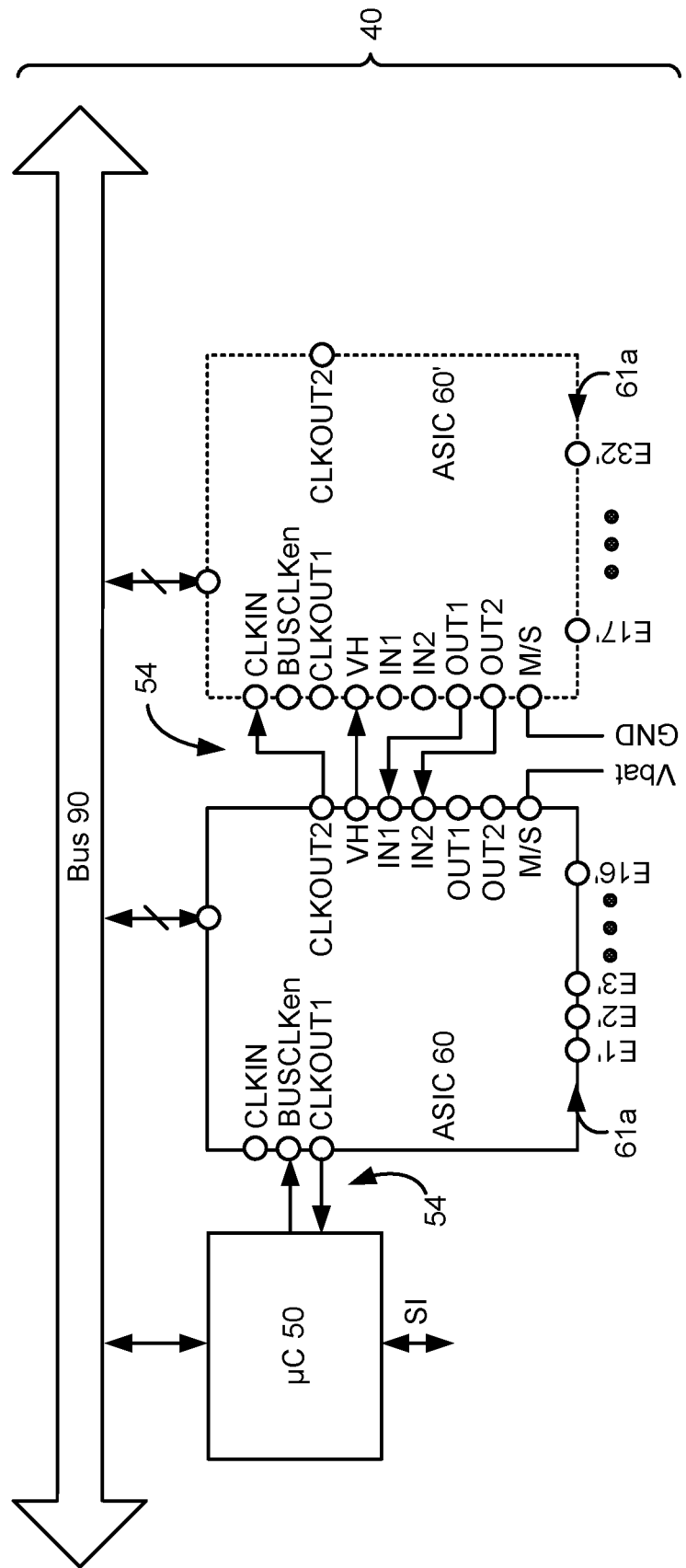
FIG. 2A shows an architecture for an IPG utilizing a microcontroller integrated circuit and an Application Specific Integrated Circuit (ASIC), in accordance with the prior art.
Figure 2B:
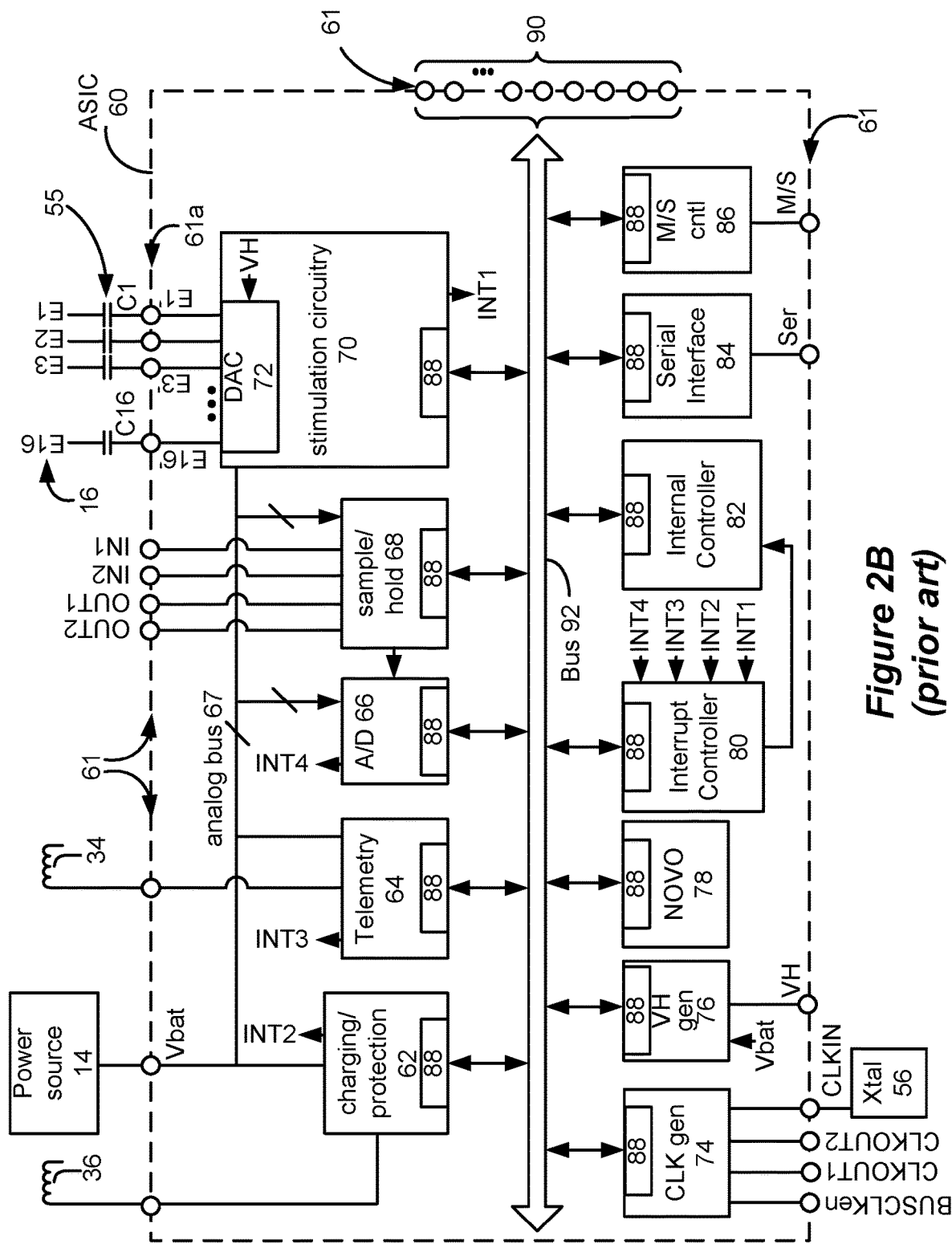
FIG. 2B shows circuitry blocks within the ASIC, and connection to off-chip components, in accordance with the prior art.
Figure 3:
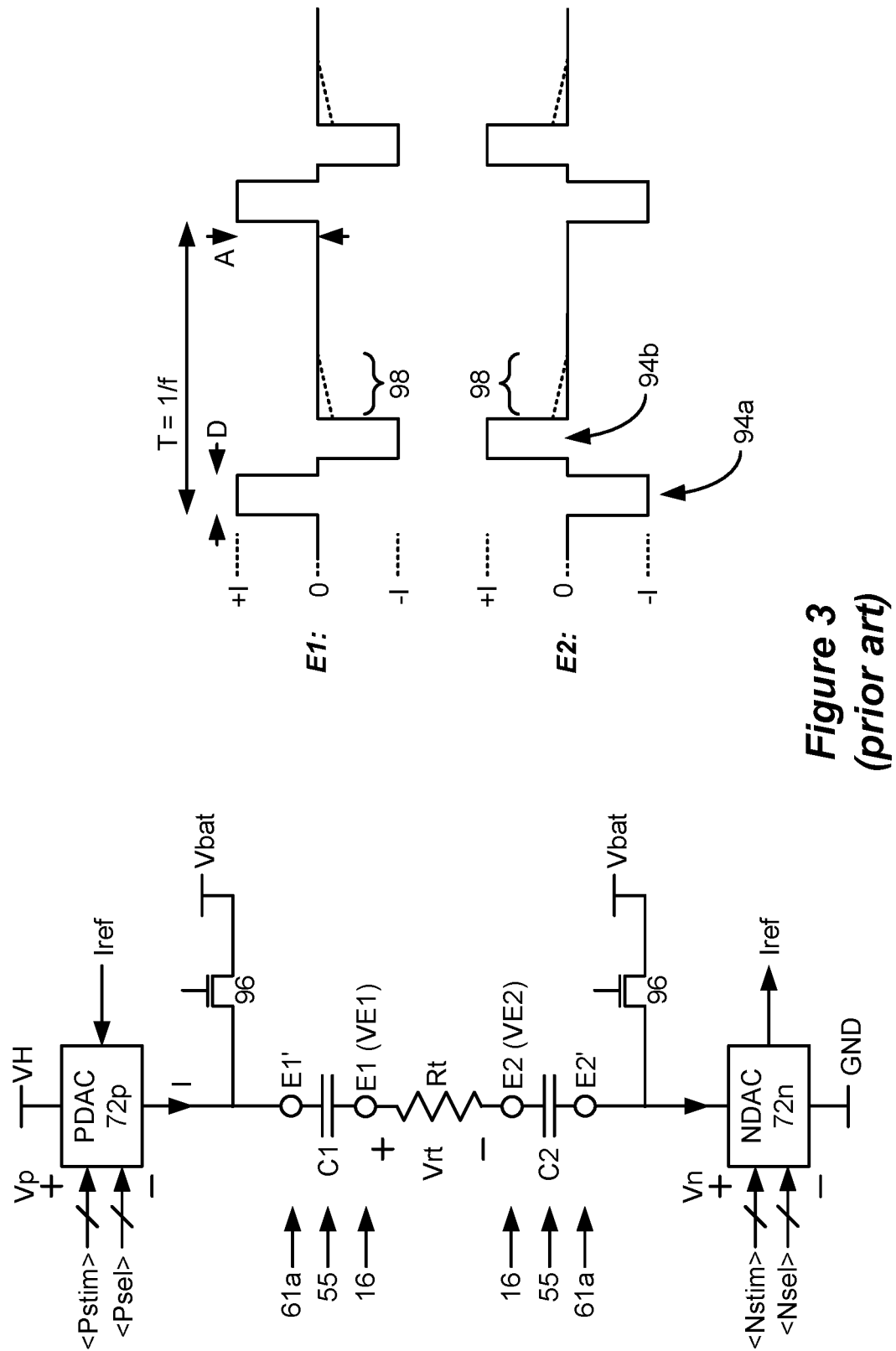
FIG. 3 shows aspects of the Digital-to-Analog converters (DACs) within the stimulation circuitry of the ASIC, and stimulation pulses formable thereby, in accordance with the prior art.

Improved ASIC 160 includes a microcontroller block 150 as part of its monolithic structure, which as shown in FIG. 4B can communicate with other functional blocks in the ASIC 160 via internal bus 192. Because ASIC 160 includes an internal microcontroller 150, an external microcontroller (e.g., 50, FIG. 2A) can be dispensed with in the improved architecture 140, simplifying IPG design and saving room within the interior of the case 12 and on the IPG's PCB 30 (FIG. 1C).

Microcontroller block 150 may receive interrupts independent of the bus 92 and its communication protocol, although interrupts may also be sent to the microcontroller 150 via the bus 92 as well. Even though ASIC 160 includes a microcontroller block 150, the ASIC 160 may still couple to an external bus 90, as shown in FIG. 4A. This can facilitate communications between the ASIC 160 and another device, such as a memory integrated circuit (not shown) or possibly another microcontroller device that might be coupled to the bus 90. Bus 90 can also facilitate communication between (master) ASIC 160 and another identically-constructed (slave) ASIC 160', shown in dotted lines in FIG. 4A. As described in the Background (FIG. 2A), use of an additional ASIC 160' allows the number of electrodes 16 the IPG 10 supports to be doubled, and many of the same off-bus connections 54 can be used as described earlier, and as described in the above-referenced ASIC Publications. In one example, the microcontroller block 150 can comprise circuitry from an ARM Cortex-M0+ Processor, which may be incorporated into the monolithic integrated circuit of the ASIC 160 by licensing various necessary circuits from the library that comprises that processor.

Figure 5A:
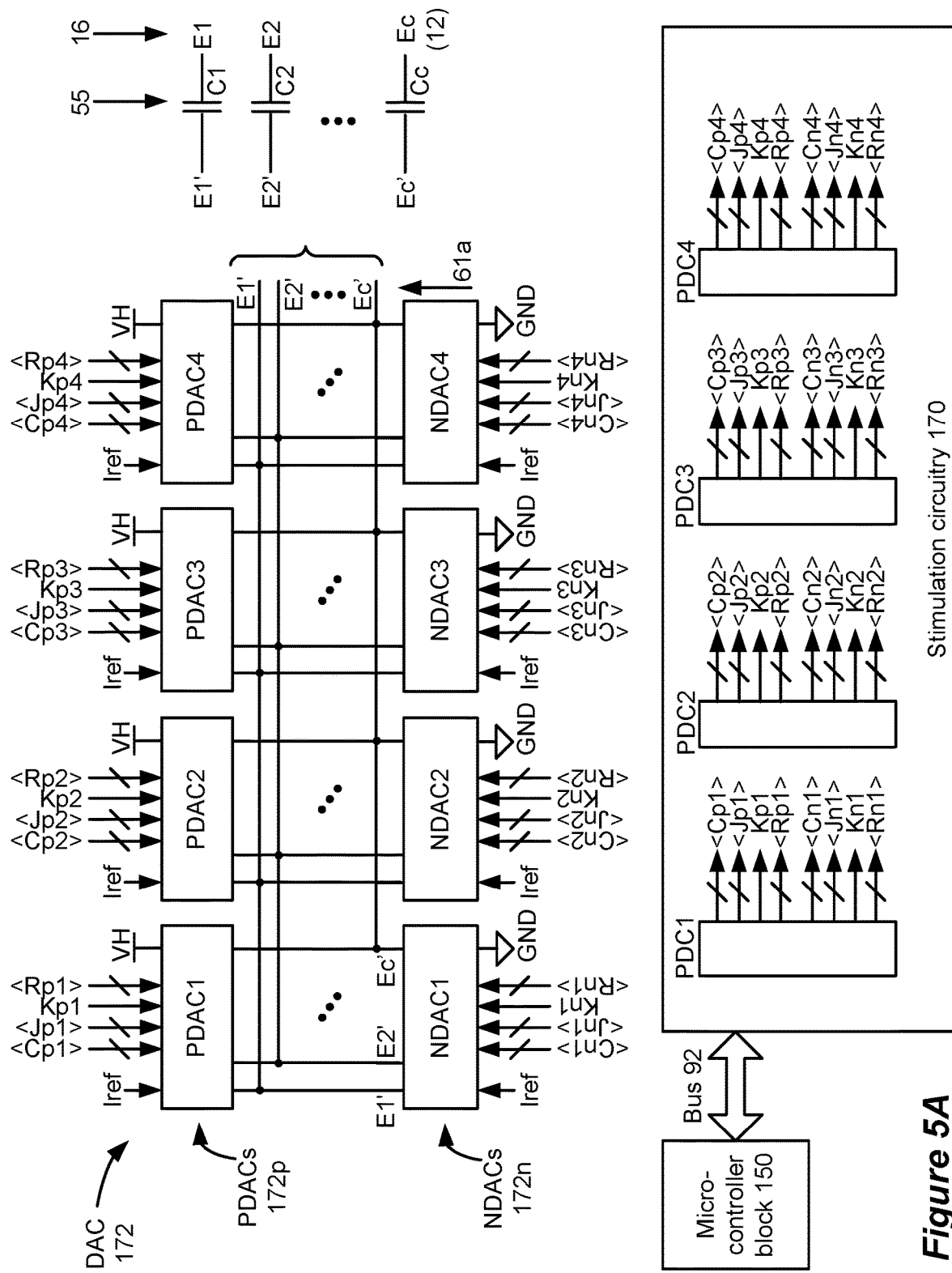
FIG. 5A shows a block level diagram of the improved DAC circuitry, which uses pairs of PDACs/NDACs each controlled by a pulse definition circuit (PDC) to form pulses in different timing channels, in accordance with an example of the invention.

FIGS. 5A-5F describe details of improved stimulation circuitry 170, including improved DAC circuitry 172. Starting with FIG. 5A, pulse definition circuits (PDCs) are provided in stimulation circuitry 170, each of which is used to define pulsed stimulation waveforms that may be issued by the DAC circuitry 172 in a timing channel (TC). In the example shown, there are four PDCs (PDC1-4), each of which contains registers populated with data by microcontroller block 150 via bus 92 to define pulses of different amplitudes, durations, and frequencies, as well as the electrodes 16 that are to be active, as shown in the example of FIG. 6. The pulses in each timing channel may run concurrently as shown, and while the pulses are shown in FIG. 6 as simple constant current, biphasic pulses, pulses of more complicated shapes and arrangements are possible. Pulses in different timing channels may overlap in time, although arbitration may be necessary if a particular electrode is to be active in more than one timing channel. Details concerning software and hardware used to populate the PDCs are disclosed in detail in U.S. Provisional Patent Application Ser. No. 62/386,000, entitled "Pulse Definition Circuitry for Creating Stimulation Waveforms in an Implantable Pulse Generator," by inventors Philip Weiss, Goran Marnfeldt, and David Wagenbach, filed Sep. 10, 2016, and is incorporated by reference in its entirety.

PDCs 1-4 issue various control signals to the DAC circuitry 172 to form the stimulation pulses in timing channels TC1-4. In a standard current mode, explained further below, each of the PDC 1-4 issues its control signals to specific portions of DAC circuitry 172. In this regard, note that DAC circuitry 172 is divided into a PDAC section 172$p$ including four PDACs 1-4, and a NDAC section 172$n$ including four NDACs 1-4. Other numbers of PDAC and NDACs could also be used.

A first PDC1 is associated with a first PDAC/NDAC pair (PDAC1/NDAC1), and sends control signals to that pair. Specifically, PDC1 sends control signals <Cp1>, <Jp1>, Kp1, and <Rp1> to PDAC1, and control signals <Cn1>, <Jn1>, Kn1, and <Rn1> to NDAC1. Similarly, PDC2 is associated with a second PDAC/NDAC pair (PDAC2/NDAC2), and sends control signals <Cp2>, <Jp2>, Kp2, and <Rp2> to PDAC2, and control signals <Cn2>, <Jn2>, Kn2, and <Rn2> to NDAC2, etc. In short, in a standard current mode of operation, each PDCx controls a designated PDACx/NDACx pair to form a timing channel of stimulation pulses at selected electrodes.

In a preferred embodiment, each of the PDACs 1-4 are coupled to a first reference voltage, preferably the compliance voltage VH as explained earlier, which is formed at the compliance voltage generator block 76 on the ASIC 160 (FIG. 4B). The NDACs 1-4 are coupled to a second reference voltage, preferably ground (GND). The voltage between the first and second reference voltages provide the power for the PDACs and NDACs to operate, with the patient's tissue intervening between them. Alternatively, each PDACx/NDACx pair could be powered by its own compliance voltage VHx, although this isn't shown. In a preferred example, the PDACs 1-4 include a lower power supply voltage Vssh below VH, and the NDACs 1-4 include a higher power supply voltage Vcc above ground, but this is explained later with reference to FIGS. 13A-14D.

Referring again to FIG. 4B, notice that ASIC 160 includes sixteen electrode nodes (E1'-E≠') 61$a$ that ultimately connect to the sixteen electrodes (E1-E16) 16 on the lead(s) 18, plus an additional electrode node 61a Ec' that ultimately connects to the IPG 10's conductive case 12. This allows the case 12 to also operate as a tissue-stimulating electrode similarly to electrodes E1-E16. ASIC 160 may support other numbers or types of electrode nodes/electrodes (e.g., thirty-two electrodes 16 plus the case 12).

As described in the Background, DC-blocking capacitors 55 are placed in series in each of the electrode output paths between the electrode nodes 61a and the electrodes 16. DAC circuitry 172 can further include passive recovery switches connected to each electrode node 61a (not shown), as is explained in further detail in U.S. Provisional Patent Application Ser. No. 62/393,007, entitled "Passive Charge Recovery Circuitry for an Implantable Medical Device," by inventors Emanuel Feldman, Goran N. Marnfeldt, and Jordi Parramon, filed Sep. 10, 2016, and which is incorporated by reference in its entirety.

Referring again to FIG. 5A, notice that corresponding electrode nodes 61a of each of the PDACs 1-4 and each of the NDACs 1-4 are connected together prior to connection to the DC-blocking capacitors 55. This allows any of the PDACs 1-4 to source a current to any one or more of the electrode nodes 61a (thus establishing one or more anode electrodes 16) and any of the NDACs 1-4 to sink a current from any one or more of the electrode nodes (thus establishing one or more cathode electrodes).

Figure 5B:
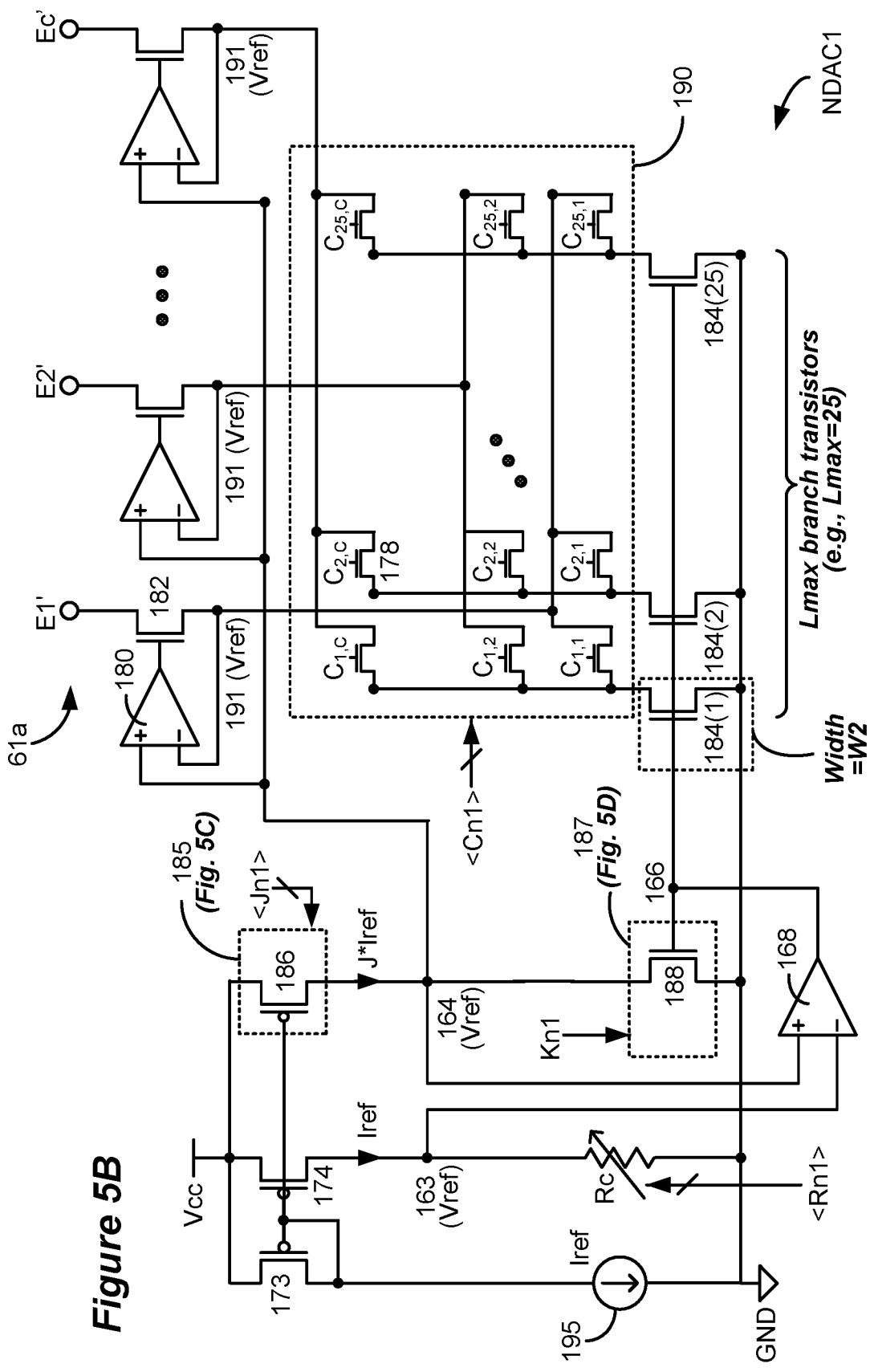
FIG. 5B shows the circuitry details in one of the NDACs, which includes various current branches controllable by a switch matrix, in accordance with an example of the invention.
Figure 6:
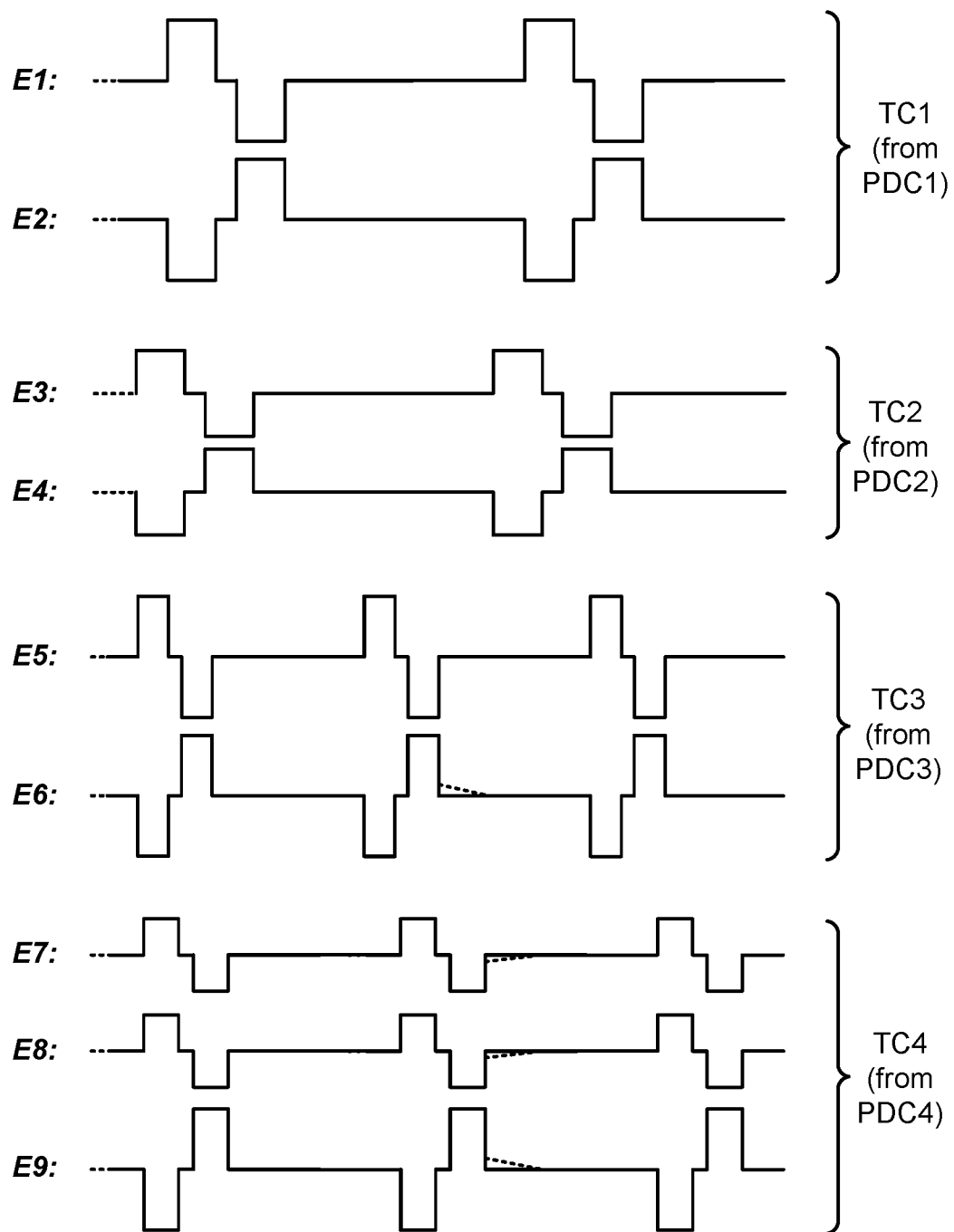
FIG. 6 shows the formation of stimulation pulses in timing channels each formed using one of the PDAC/NDAC pairs, in accordance with an example of the invention.

FIG. 5B shows the circuitry for one of the NDACs (NDAC1) used to sink current from one or more selected electrode nodes 61a. NDAC1 receives control signals <Rn1>, <Jn1>, Kn1, <Cn1> from its associated PDC1 as noted earlier. NDACs 2-4 would be similar in construction, although they can receive different control signals from their PDCs 2-4, as shown in FIG. 5A.

A reference current Iref provided by a reference current source 195 is input to NDAC1. Note in FIG. 5A that this reference current Iref can be provided to each of the NDACs 1-4 and PDACs 1-4. Alternatively, each NDAC and each PDAC can be provided with its own unique reference current. Still alternatively, all NDACs 1-4 can be provided with one reference current, and all PDACs 1-4 can be provided with another reference current.

Referring again to FIG. 5B, the reference current Iref is mirrored by a well-known current mirror configuration from transistor 173 into a transistor 174 that meets with a reference resistor, Rc. Specifically, the current from current source 195 is mirrored from transistor 173 to transistor 174 by connecting the gates of these transistors, and by connecting these gates to the current source 195 as shown. In a preferred example, reference resistor Rc is a variable resistor whose value may be set by one or more control signals <Rn1> issued by PDC1. Control signals <Rn1> may be used to trim the value of Rc, with the control signals being used to include or exclude various resistors in a resistor network comprising Rc to change its resistance, as is well known.

Providing Iref into resistance Rc establishes a voltage, Vref, at node 163 (Vref=Iref*Rc). In a preferred embodiment, Vref equals 100 mV, and Rc may be trimmed to tailor the value of Vref. Adjustment of Rc may be particularly useful should there be process variations inherent in fabrication of the wafers used to fabricate the monolithic ASICs 160. It is contemplated that Rc would be adjusted per <Rn1> after initial fabrication, and left constant thereafter. However, Rc could also be adjusted over the lifetime of the IPG 10 containing the ASIC 160.

The reference current Iref is further current mirrored from transistor 173 into transistor(s) 186 in circuit 185 to produce an amplified current J*Iref at node 164. The value of the scalar J depends on the number of transistors 186 that are selectively included in the current mirror, which is adjustable in accordance with control signals <Jn1> provided by PCC1. Because circuit 185 sets an analog current J*Iref in accordance with digital control signals <Jn1>, circuit 185 itself comprises a DAC within each PDAC1-4 and each NDAC1-4, and is referred to in each as a "master DAC" 185. However, the current provided by the master DAC 185 (J*Iref) is preferably amplified again before presentation to the electrode nodes 61a, as explained later.

A couple of examples of master DACs 185 are shown in further detail in FIG. 5C. In the top example, master DAC 185 is controlled directly by eight control signals <Jn1>, Jn1(1) to Jn1(8). Each of these control signals is input to a selection transistor 192, each of which is in series with a differing number of current mirror transistors 186. The number of current mirror transistors 186 varies in binary fashion, such that Jn1(1) controls connection of one transistor 186; Jn1(2) controls connection of two transistors 186; Jn1(3) controls connection of four transistors 186, and so on, with Jn1(8) controlling connection of 128 transistors 186. Thus, control signals <Jn1> allow mirrored current Iref to be amplified, and output to node 164 in units ranging from Iref (J=1, when <Jn1>=11111110) to 255*Iref (Jmax=255, when <Jn1>=00000000). (Note that because selection transistors 186 are P-channel transistors, they are active low). For example, if the control signals <Jn1>=11101010 (the inverse of the number 21 in binary), only (16+4+1)*Iref will be mirrored at node 164 for a total current 21*Iref (J=21).

In the bottom example of FIG. 5C, master DAC 185 includes logic circuitry 193, which converts the eight control signals <Jn1> into 256 different control signals j0 to j255. Control signals j1-j255 are each sent to one of the selection transistors 192, each of which is in series with only a single current mirror transistor 186. The assertion of each control signal jx adds Iref to the total current at node 164, with logic circuitry 193 asserting an appropriate number of the control signals jx that corresponds with control signals <Jn1>. For example, if the same control signals <Jn1>=11101010 described above are asserted, logic circuitry 193 will assert j1-j21 and j22-j255 will be deasserted, again producing a total current at node 164 of 21*Iref.

Referring again to FIG. 5B, amplified current J*Iref as output from master DAC 185 at node 164 passes through a resistance block 187, formed in this example by M (e.g., four) resistance transistors 188, as shown in FIG. 5D. Included in series with each resistance transistor 188 is a selection transistor 194, one of which is always on, as its gate is tied to a high logic state, such as Vcc. A control signal Kn1 controls the other selection transistors 194. Kn1 is normally not asserted in the standard current mode, and therefore resistance block 187 normally activates only a single resistance transistor 188 in the standard current mode (FIG. 5E). Kn1 is however normally asserted in a high resolution current mode, which places all M resistance transistors 188 in parallel (FIG. 5F). Note that each resistance transistor 188 can be fabricated with a width (W1) that sets its on resistance, although transistor length can also be adjusted to adjust the resistance of transistors 188. It should be noted that resistances other than transistors 188 could be used in the resistance block 187.

Referring again to FIG. 5B, the gates of resistance transistors 188 in the resistance block 187 are connected at node 166 to the gates of several (Lmax) branch transistors 184, each of which is connected to a column of switches 178 in switch matrix 190. Notice that resistance transistors 188 and branch transistors 184 are not coupled in a current mirror configuration (gate node 166 is not coupled to node 164 as would occur in a current mirror configuration; compare transistors 173 and 174). Rows of the switches 178 in the switch matrix 190 are connected to nodes 191 in each of the electrode nodes' output paths. In the example shown, there are Lmax=25 branch transistors 184, and 17 electrodes nodes (E1'-E16' and Ec'), and thus switch matrix 190 comprises 25×17 switches 178 and 25×17 control signals <Cn1> to control each. Differing numbers of branch transistors and electrode nodes could also be used. Resistances other than transistors 184 could be used for each of the branches.

In a preferred example, each of the branch transistors 184 is sized relative to the resistance transistors 188 of the resistance block 187 to set a resistance difference between them. For example, while resistance transistors 188 in the resistor block 187 are fabricated with a width of W1, each of the branch transistors 184 is fabricated with a width W2, which is preferably wider than W1. Hence, each resistance transistor 188 is W2/W1 times more resistive than each branch transistors 184.

Further included in NDAC1 are operational amplifiers 168 and 180. Operational amplifier 168 receives node 163 at one of its inputs, which as mentioned earlier is set to Vref. The output of operational amplifier 168 is connected to node 166, which is connected to the gates of the resistance transistors 188 and the branch transistors 184 to turn them on. Through feedback through the resistance transistors 188, operational amplifier 168 will force its other input, node 164, to match the input at node 163. Thus, because node 163 is held to Vref, so too is node 164 held to Vref.

Node 164 is input to further operational amplifiers 180, each of which controls an output transistor 182 though which current flows to or from one of the electrodes node 61a via an electrode output path. The other inputs to the operational amplifiers, nodes 191, are connected to opposite sides of the output transistors 182 from the electrode nodes 61a. Through feedback through the output transistors 182, the operational amplifiers 180 will force input nodes 191 to match input node 164, which as just noted is held at Vref. Thus, nodes 191 are also held at Vref.

Switch matrix 190 allows current to be provided to one or more selected electrodes based on the status of switch matrix control signals <Cn1>. Quantifying the value of the provided current is explained subsequently, but for now it can be assumed that each branch transistors 184 provides a single "unit" of current. For example, assume it is desired to sink three units of current from electrode E2. (Again, an NDAC1 is illustrated in FIG. 5B, but one of the PDACs (see FIG. 7) would source units of current to the electrodes). This can be accomplished by asserting any L=3 of the control signals <Cn1> in the switching matrix 190 (e.g., $C_{1,2}$, $C_{2,2}$, and $C_{3,2}$) that connect to electrode node E2' (note that any three control signals $C_{X,2}$ could be asserted). This closes the switches 178 associated with these control signals, and allows L=3 branch transistors (e.g., 184(1), 184(2) and 184(3)) to each sink a unit of current from E2'. Thus, in sum, three units of current are sunk from electrode node E2' and hence electrode E2.

FIGS. 5E and 5F explain this in further detail, and also assist in quantifying the amount of current provided by each of the branch transistors 184. FIG. 5E explains current flow when Kn1=0 (which normally comprises the standard current mode), while FIG. 5F explains current flow when Kn1=1 (which normally comprises the high resolution current mode). Both FIGS. 5E and 5F show only portions of the NDAC1 circuitry for simplicity, and in both figures it is assumed that only L=3 branches are used to sink current from electrode node E2' (via assertion of control signals $C_{1,2}$, $C_{2,2}$, and $C_{3,2}$). Further, both figures assume that the master DAC 185 has been set by control signal <Jn1> to produce a current of J*Iref.

In FIG. 5E, only one of M resistance transistors 188 is active in resistor block 187 (FIG. 5D), because Kn1=0 defeats activation of the other resistance transistors 188, which are crossed out in FIG. 5E. The resistance of the selection transistor 194 in the active resistance circuit 187 (FIG. 5D) is negligible compared to the resistance provided by the active resistance transistor 188. As a result, Vref at node 164 is effectively dropped across the resistance transistor 188 (from its drain to its source). This drain to source voltage Vds across resistance transistor 188 is shown for accuracy as Vref', but Vref'≈Vref=100 mV because selection transistor 194 is negligible. Current J*Iref flows through the resistance transistor 188 from the master DAC 185 at a voltage of Vref across the resistance transistor 188. Therefore, the resistance of the active resistance transistor 188 in FIG. 5E equals Vref/(J*Iref). Note that op amp 168 will set node 166 to a voltage V2 necessary to bring resistance transistor 188 to this resistance.

As discussed earlier, each resistance transistor 188 has a width W1 relative to the width W2 of each of the branch transistors 184. Because the gates of the active resistance transistor 188 and the branch transistors 184 are biased to the same voltage (V2) at node 166, transistors 184 are on to the same extent as the active resistance transistor 188. However, because branch transistors 184 are wider, they will be less resistive than transistor 188 by a factor of W2/W1. Therefore, the resistance of each of the branch transistors 184 will be (Vref'*W1)/(W2*J*Iref).

The voltage drop across the branch transistors 184 are held to Vref' just the like active resistance transistor 188. Remember that each of the nodes 191 is held at Vref. Vref is therefore dropped across the series connection of the selected switches 178 in the switch matrix 190 and the active branch transistors 184. However, similar to the selection switches 194 in the resistance block 187, the resistance across the switches 178 is negligible compared to the resistance of the branch transistors 184. As a result, Vref at nodes 191 are effectively dropped from the drain to the source of the branch transistors 184. Again, this drain to source voltage Vds across the branch transistors 184 is shown for accuracy as Vref', but again Vref'≈Vref=100 mV because the switches 178 are negligible. Further, the selection transistors 194 and switches can be sized to drop an equal negligible voltage drop, so that the Vds drop across the branch transistors 184 equals that across the active resistance transistor 188 (Vref').

Therefore, the current through each of the branch transistors 184 (Ib) can be calculated by dividing the voltage (Vref') across each branch transistor 184 by its calculated resistance (Vref'*W1)/(W2*J*Iref), which equals Ib=(W2*J*Iref)/W1. Because W2 is preferably larger than W1, notice that the current provided by the master DAC 185 (J*Iref) is amplified by a factor of W2/W1 in each of the branches.

The currents Ib formed in each of the L=3 active branches are then summed at node 191 associated with selected electrode node E2', and passed through its output transistor 182, providing a total current at electrode node E2' of I=(L*W2*J*Iref)/W1. Although not shown, these currents would be negative, as they sink current from selected cathode electrode E2.

In FIG. 5F, control signal Kn1 is asserted as generally (but not necessarily) occurs in the high resolution current mode.

(Kn1 can also be asserted as a more general means of control of NDAC1 in the standard current mode). When Kn1 is asserted, all M resistance transistors 188 are selected in resistance block 187. Because these transistors 188 are in parallel, their effective combined width is M*W1. Note however that the total resistance of transistors 188 is still Vref'/(J*Iref), because neither the current from the master DAC 185 (J*Iref) nor the voltage dropped across the transistors (Vref') has changed. Keeping the total resistance of all M resistance transistors 188 to Vref'/(J*Iref) is achieved by the op amp 168, which drops the voltage at node 166 slightly (V1<V2) so that the resistance transistors 188 are slightly less "on" than when only a single transistor 188 is used (FIG. 5E).

The branch transistors 184 will be on to the same degree as the resistance transistors 188, but transistors 184 will be less resistive than the resistance transistors 188 by a factor of W2/(M*W1). Therefore, the resistance of each of the branch transistors 184 will be R=(Vref'*M*W1)/(W2*J*Iref). Because the voltage drop across the branch transistors 184 is the same as across the resistance transistors 188 (Vref') as explained earlier, the current through each of the branch transistors 184 equals Ib=(W2*J*Iref)/(M*W1). Preferably, W2, W1, and M are chosen such that the current provided by the master DAC 185 (J*Iref) is amplified in each of the branches, although note that this amplification is reduced by a factor of 1/M in each of the branches of FIG. 5F compared to FIG. 5E. When summed together at node 191, total current passed though output transistor 182 to the selected electrode node is I=(L*W2*J*Iref)/(M*W1).

Exemplary values assist in understanding NDAC1's operation, and the magnitudes of the various currents it produces. Assume for example that Iref=−0.1 microamps. This allows the master DAC 185 to amplify Iref and to produce output currents (J*Iref) of −0.1, −0.2, −0.3, . . . −25.5 microamps, depending on the value of the <Jn1> control signals (J), and assuming a maximum value of Jmax=255.

When Kn1 is not asserted (FIG. 5E) as usually occurs in the standard current mode, assume that the width W2 of the branch transistors 184 are 40 times the width W1 of the active resistance transistor 188 in the resistance block 187 (i.e., W2/W1=40). Each branch transistors 184 will amplify the master DAC 185' current by this ratio, and thus be able to provide currents of Ib=−4, −8, −12, . . . −1020 microamps (again, depending on J). If it is assumed that all branches are selected (L=Lmax=25), NDAC1 can produce a summed value of I=−0.1, −0.2, −0.3, . . . −25.5 mA. I=Imax=−25.5 mA comprises the total current NDAC1 can produce, when J provided by the master DAC 185 equals Jmax=255, and the number of selected branches (i.e., the number of selected switch matrix switches 178) equals Lmax=25. This summed value can be presented to one anode electrode or shared by more than one anode electrode, as explained further below.

When Kn1 is asserted (FIG. 5F) as usually occurs in the high resolution current mode, the branch currents are further scaled by a factor of 1/M (e.g., ¼), where M equals the number of active resistance transistors 188 in the resistance block 187. Thus, using the same values as above, each branch transistor 184 will be able to provide currents of Ib=−1, −2, −3, . . . −255 microamps (depending on J), and the summed value of the branch currents (again assuming all Lmax=25 branches are selected) is I=−0.025, −0.05, −0.075, . . . −6.375 mA, with Imax=−6.375 mA.

It should be noted that the reference current (Iref), the maximum amount by which the reference current can be amplified by the master DAC 182 (Jmax), the number of transistors in the resistance block 187 (M), the relative widths of the resistance transistors 188 and the branch transistor 184 (W1 and W2), or their relative resistance more generally, and the maximum number of branches (Lmax) can all be adjusted in different designs.

Figure 7:
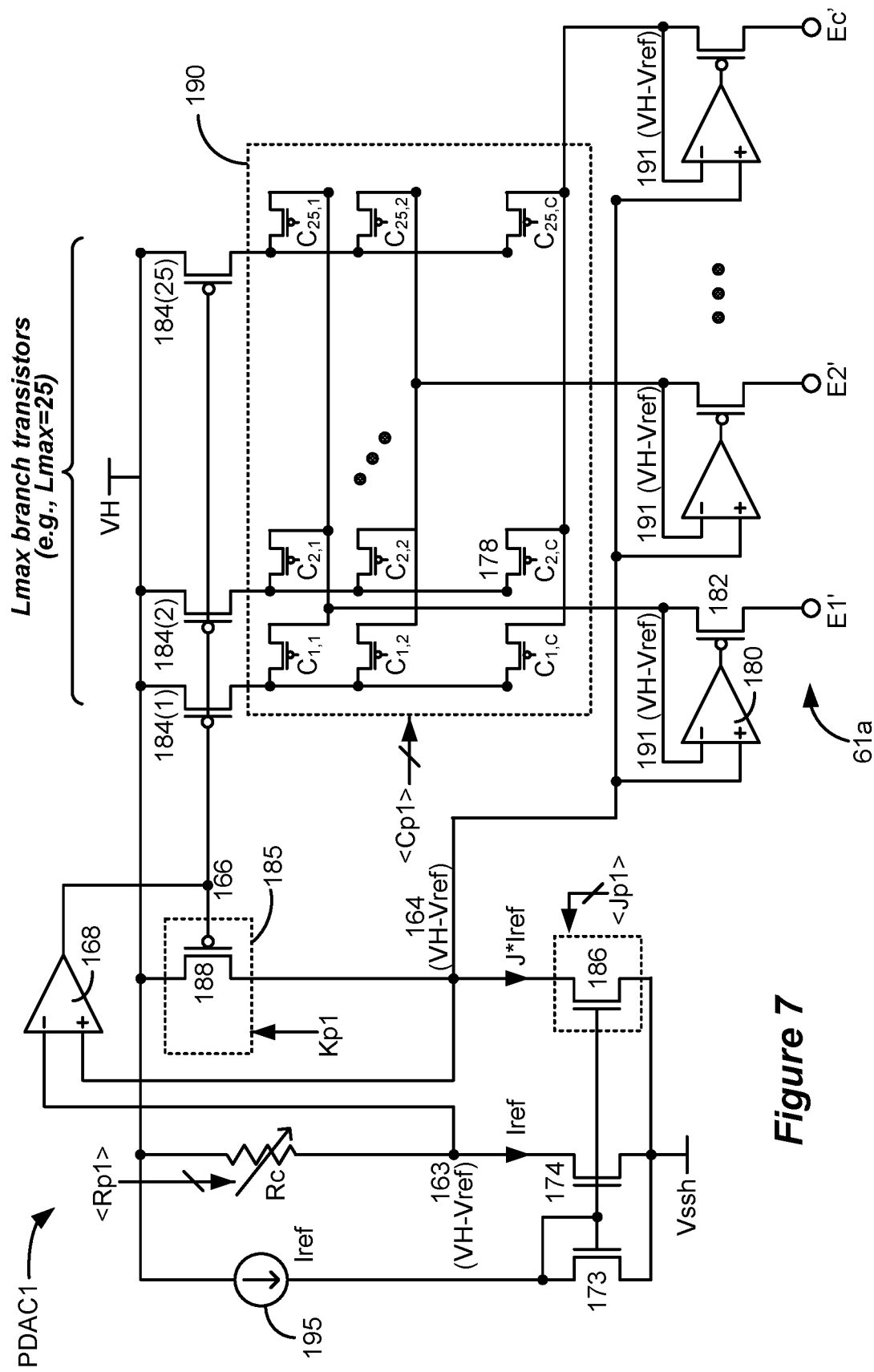
FIG. 7 shows the circuitry details in one of the PDACs, which is generally similar to but inverted from the NDAC described earlier, in accordance with an example of the invention.

FIG. 7 shows an example of one of the PDACs (PDAC1). As one skilled in the art will appreciate, the circuitry for PDAC1 is largely "inverted" from that shown for NDAC1 in FIG. 5B, and has expected differences given its difference in polarity. For example, current-producing portions of PDAC1 are coupled to the compliance voltage VH instead of ground, thus allowing the PDAC to source current to selected electrode nodes 61a, allowing their electrode 16 to operate as anodes (positive current). Further, many of the transistors comprise P-channel devices instead of N-channel devices as appear in the NDACs. Otherwise, the PDACs will function similarly to the NDACs, and have analogous control signals to those described earlier (although the control signals may be active at a different logic state). For simplicity, elements of PDAC1 in FIG. 7 are labeled with elements numerals that correspond to analogous elements in the NDAC1 of FIG. 5B. Notice that the reference voltage used by the PDACs (formed by reference transistor Rc) comprises VH-Vref. This reference voltage will vary because, as explained in the Background, VH varies to keep the PDACs and NDACs operating at a power-efficient level. Further implications stemming from the variability of the compliance voltage VH are discussed later in conjunction with FIGS. 13A-14D.

The NDACs 1-4 and PDACs 1-4 provide a significant degree of flexibility to how stimulation currents may be provided at the electrodes. As mentioned earlier, each PDAC/NDAC pair can and its associated pulse definition circuit (PDC) can in the standard current mode form pulses in a timing channel independent of those formed by other pairs (FIG. 6). Further, there are several manners in which the PDACs/NDACs can be controlled to produce currents of desired magnitudes at an electrode. Assume for example that it is desired to form a (sink) current of −4.0 mA at electrode E5, using the example values for the various parameters used earlier (Iref=−0.1 microamps; Jmax=255; M=4; W2/W1=40; Lmax=25). All of the following combinations of control signals (there are others) would yield the desired current I=−4.0 mA at electrode E5:

| J | Kn1 | Number of active branches L (number of $C_{x,5}$ asserted) |
|---|---|---|
| 40 | 0 | 25 |
| 100 | 0 | 10 |
| 160 | 1 | 25 |
| 200 | 1 | 20 |

Figure 8:
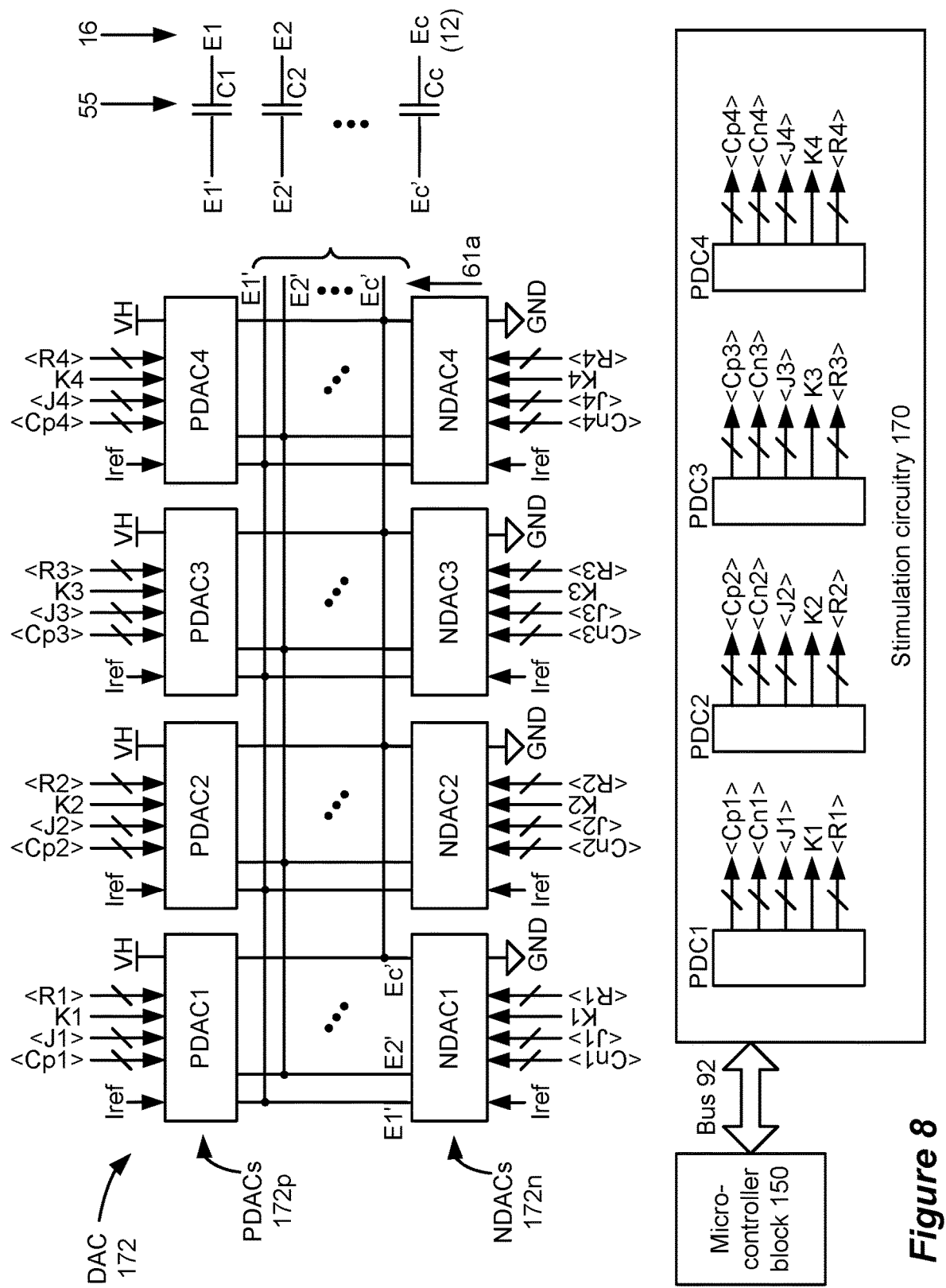
FIG. 8 shows unification of the some of the control signals issued by each PDC to its PDAC/NDAC pair, in accordance with an example of the invention.

In an actual implementation, it might be expected that each pulse definition circuit (PDC) would control its associated PDAC and NDAC similarly, and as a result, the control signals issued by each PDC may be simplified, as shown in FIG. 8. In this example, each PDC issues only one K control signal to each resistance block 187 (FIG. 5B) in its PDAC/NDAC pair. Thus, as shown, PDC1 issues control signal K1 to its PDAC1 and NDAC1; PDC2 issues control signal K2 to its PDAC2 and NDAC2, etc. Similarly, each PDC issues only one set of J control signal to set the current provided by the master DAC 185 in its PDAC/NDAC pair. Thus, as shown, PDC1 issues control signals <J1> to its PDAC1 and NDAC1; PDC2 issues control signals <J2> to its PDAC2 and NDAC2, etc. Resistance control signals <R> may also be unified for each PDAC/NDAC pair. In reality, these control signals K, <J>, and <R> may be inverted at one of the DACs in each pair given their different polarities. Preferably, the switch matrix control signals issued from each PDC for its associated PDAC and NDAC, e.g., <Cp1> and <Cn1> remain separate so that different electrodes can be chosen to receives the source and sink currents respectively.

Such unified control of each PDAC/NDAC pair is sensible—particularly as concerns control signals K and <J>—as this allows each DAC in a pair to provide the same amplification of the reference current Iref, and hence allows the PDAC/NDAC pair to provide the same current, +I/−I. This is logical, as the source current and sink current in each PDAC/NDAC pair should match to ensure that the current sourced to the tissue Rt matches the current sunk from the tissue in each timing channel.

Further, it can be desirable that the maximum current be used in each PDAC/NDAC pair. This occurs by selecting all Lmax=25 branches by appropriate assertion of the <Cp1> and <Cn1> control signals. This allows +I from the PDAC to be shared between one or more selected anode electrodes, and −I to be shared between one or more selected cathode electrodes.

Figure 9A:
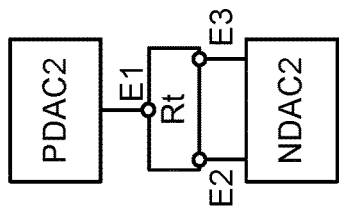
Figure 9A:
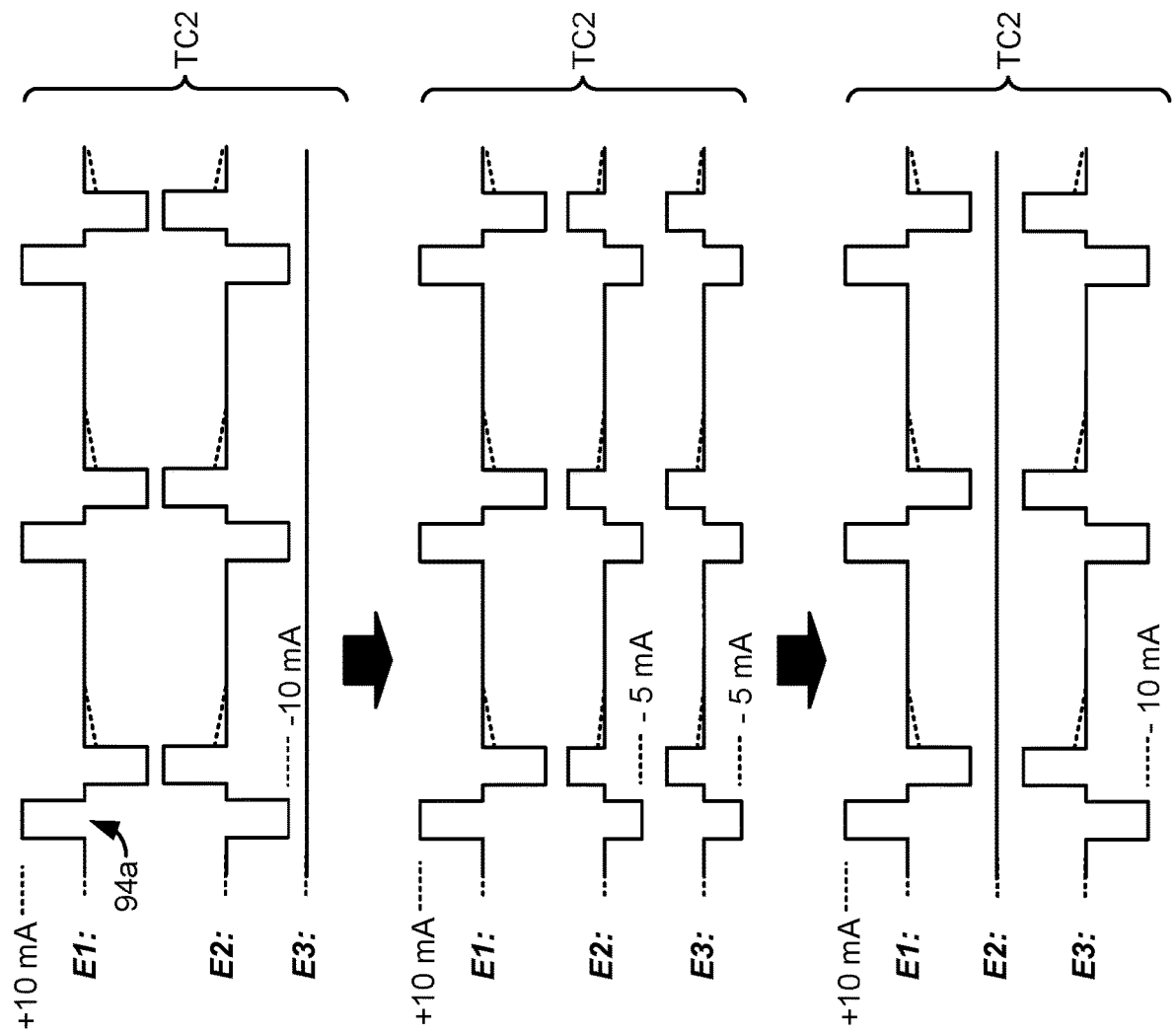

FIG. 9A shows an example of this use model in a typical context, in which current is moved in a timing channel TC2 (under control of PDC2) from one electrode (E2) to another (E3). More specifically, electrode E1 is selected as an anode (during first pulse phase 94a) to provide a sourced current of +10 mA from PDAC2. Initially, E2 is chosen as the corresponding cathode, and thus sinks −10 mA from NDAC2 to recover all of the sourced current, as shown in the top waveforms in FIG. 9A. However, over time, portions of the sink current are moved from E2 to E3. Thus, in the middle waveforms of FIG. 9A, it can be seen that half of the sink current has been moved from E2 (−5 mA) to E3 (−5 mA). This could continue as more sink current is moved to E3, and eventually E3 may sink all of E1's sourced current, with E2 sinking none, as shown in the bottom waveforms.

Moving current between electrodes in small increments is a desirable use model, particularly during fitting of the IPG 10 to a particular patient. This because it may not initially be known what electrodes should be chosen for stimulation to relieve a patient's symptoms (e.g., pain). Gradually moving current between electrodes to determine which electrodes should be active to provide therapy, and in what proportions, may be more comfortable and less dangerous for the patient. For example, if all of the sink current is moved instantaneously from E2 to E3 in the example of FIG. 9A, the effect may be jarring on the patient. Moving current in gradual increments reduces this risk, and allows finer tuning of therapy as source current can be shared by one or more selected anode electrodes, and sink current can be shared by one or more selected cathode electrodes. See U.S. Pat. No. 7,890,182, discussing this issue in further detail. As is well known, moving current in the manner shown can be performed by a clinician programmer running IPG control software in communication with a patient's IPG 10. Alternatively, current may also be movable between electrodes by the patient using a hand-holdable external controller.

FIG. 9B shows how moving current between the electrodes of FIG. 9A can be achieved. First, J2 is set to a value that will set the amplitude for +I and −I in PDAC2 and NDAC2 that match the total source and sink currents needed: +10 mA and −10 mA in this example. Assuming K2='0', a value of J=100 will produce I=+/−10 mA in PDAC2/NDAC2 if all Lmax=25 branches in these DACs are asserted.

The source current at PDAC2 isn't being moved between anode electrodes in this example, and will remain at E1. Thus, the entirety of the source current I=+10 mA is sent to anode electrode E1, which occurs by setting control signals <Cp2> such that $C_{1,1}$ to $C_{1,25}$ are all asserted. In other words, all 25 branches in PDAC2 will send their currents to anode electrode E1, which sums to +10 mA as desired.

At time t=0, the entirety of the sink current at NDAC2, I=−10 mA, is sent to cathode electrode E2, which occurs by setting control signals <Cn2> such that $C_{2,1}$ to $C_{2,25}$ are all asserted. In other words, all 25 branches in NDAC2 will send their currents to electrode E2, which sums to −10 mA as desired. None of the branches are connected to electrode E3 at this time.

At time t=1, a small amount of current has been moved from E2 to E3 (−0.4 mA), which occurs by connecting one of the branches to E3 ($C_{3,25}$). As this branch (see branch transistor 184(25) in FIG. 5B) can no longer be connected to E2, E2 only receives −9.6 mA ($C_{2,1}$ to $C_{2,24}$). This process continues, with additional branches being connected one at a time to E3 (more of $C_{3,x}$ are asserted, while less of $C_{2,x}$ are asserted), moving another increment of −0.4 mA each time. Eventually, at time t=26, it is seen that all of the branches in the NDAC2 are connected to cathode electrode E3 ($C_{3,1}$ to $C_{3,25}$) and no branches are connected to E2. Thus cathode E3 receives all of the sink current (−10 mA), and cathode E2 receives none. In short, the entirety of the sink current has been moved in −0.4 mA increments from E2 to E3. Further, because the currents in PDAC2/NDAC2 have been set to +I/−I and all Lmax=25 branches are always asserted in each, the total source current and total sink current is balanced, even though −I is shared between cathode electrodes E2 and E3 in different proportions at different times.

(It should be noted that what is really important to current balancing is that the same number of branches be used in each PDAC/NDAC pair. For example, less than Lmax=25 branches could be used in each. However, in the example shown, this would mean some number of branches is always not being used in both the PDAC and NDAC; J would have to be increased to compensate. For example, if only 20 branches are used in each (e.g., control signals $C_{21,x}$ to $C_{25,x}$ are never asserted), then J would need to be increased from 100 to 125 to allow +10/−10 mA pulses to be made).

Notice that the resolution of the current that can attained at any given electrode is determined by the maximum number of branches (Lmax) provided in the NDAC. More specifically, currents can only be formed in increments of I/Lmax. Thus, in the foregoing example, currents can only be set at the electrode in increments of +/−10 mA/25, or +/−0.4 mA (i.e., 4% of I). Thus, current cannot be divided between anodes or between cathodes in any proportion within a DAC. For example, the sink current in the example of FIG. 9A could not be split 50%/50% between cathode electrodes E2 and E3-52%/48% or 48%/%52 would be as close as could be achieved. This is generally not problematic, although it may limit the clinician who will not be able to specify currents at his clinician's programmer that are inconsistent with the IPG's resolution.

Higher resolution (smaller current increments) can be achieved by including a greater number of branches in each of the PDACs and NDACs. For example, if each PDAC and NDAC contained Lmax=100 branches, the resolution would increase to 1%. This would allow the source or sink current in the foregoing example to be moved in increments of +/−0.1 mA, and would allow greater flexibility in sharing source and sink currents between electrodes. For example, this would allow the sink current in the example of FIG. 9A to be split 50%/50% between cathode electrodes E2 and E3 (or 51%/49% for that matter).

However, a larger number of branches in each of the PDAC/NDAC pairs would take more space on the ASIC 160, and could have other disadvantages as well. One hundred branches would also increase the maximum current of each PDAC and NDAC, Imax, from +/−25.5 mA to +/−102 mA, which may too high to be safe. The compliance voltage generation block 76 that produces the compliance voltage VH power supply for the DACs may not be able to provide such a high levels of current as a practical matter.

Asserting the K control signals in a given PDAC/NDAC pair can alleviate the problem of having higher and perhaps unsafe currents. As discussed above, assertion of the K control signals increases the number of resistance transistors 188 activated in the resistance block 187 (to M), which decreases the current in each of the branches by a factor of 1/M (or ¼ in the example explained earlier). For example, if K2 is asserted in the example of FIG. 9B, the maximum current, Imax (at J=Jmax and L=Lmax) providable by PDAC2/NDAC2 will be +/−6.375 mA. This would be insufficient to form the total current −10 mA needed at cathode electrodes E2 and E3. However, if a large number of branches is also used (e.g., Lmax=100), optimal performance may be achieved. Resolution would be high (1%), and maximum current providable by each PDAC/NDAC pair would be sufficiently high but also safe (+/−25.5 mA).

Figure 10A:
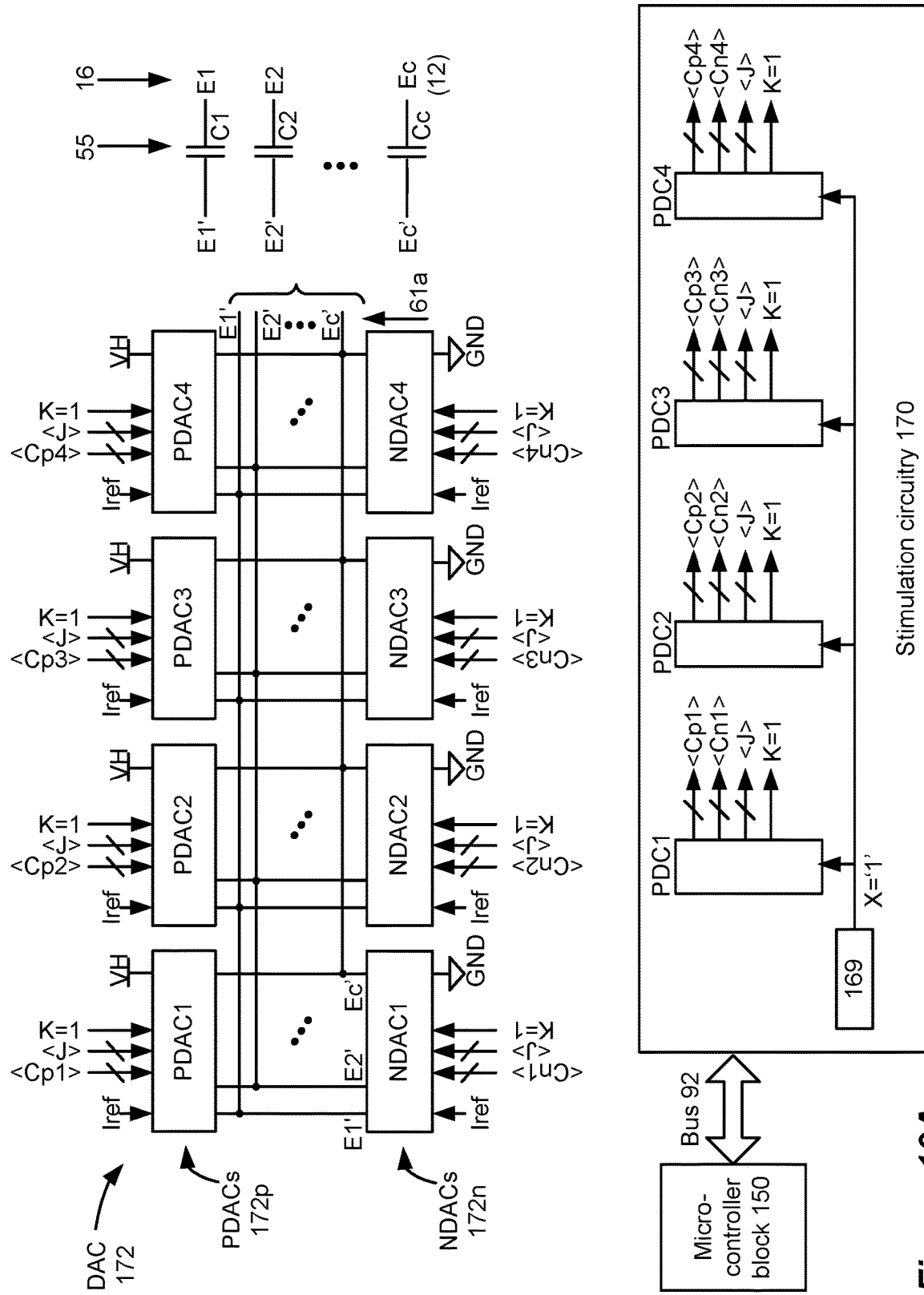
Figure 10B:
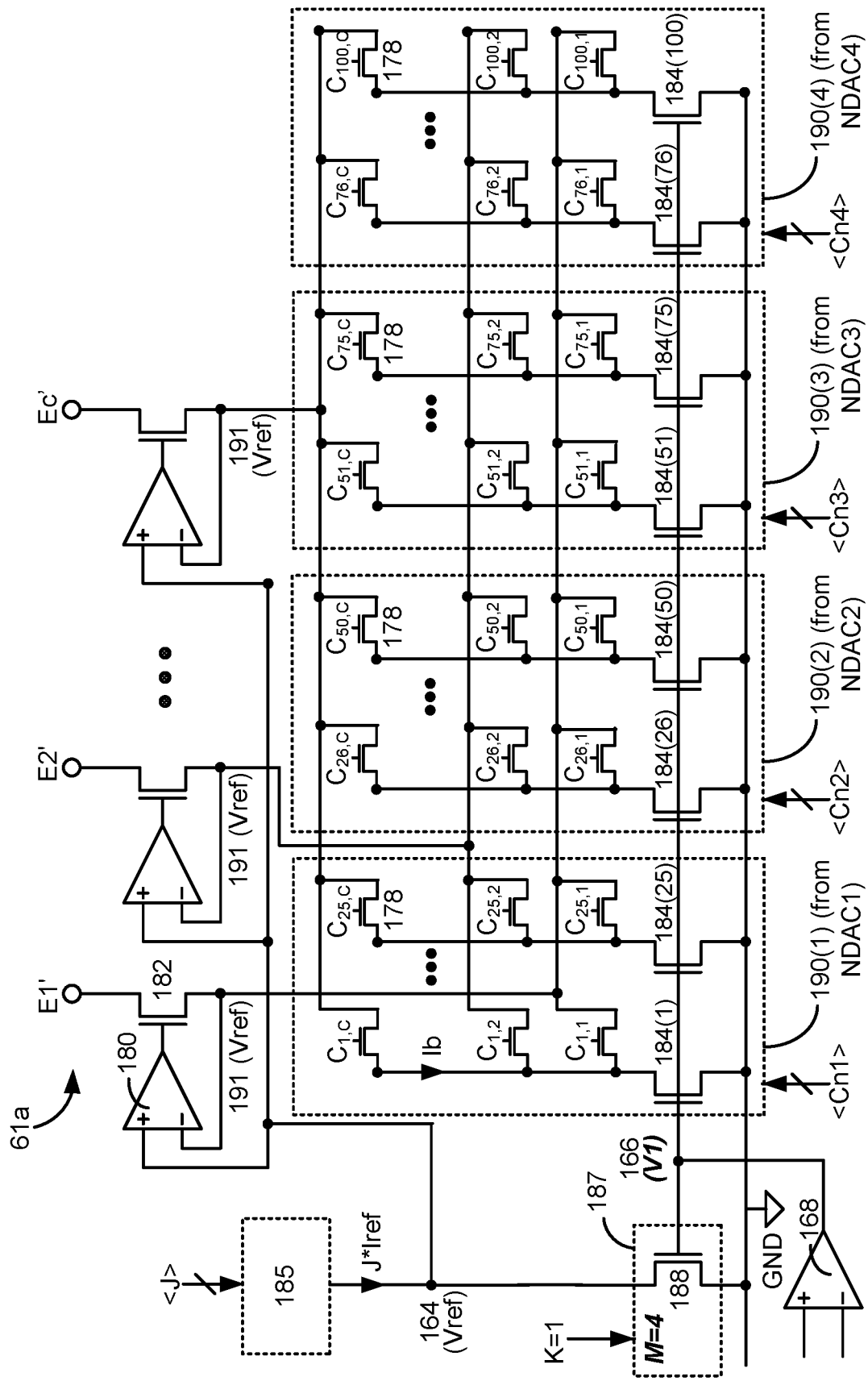

FIGS. 10A-10C show another example of this optimal solution, in what is called the high current resolution mode. This mode essentially operates as just described—the K control signals are asserted for lower current, and a larger number of branches are used for current higher resolution. However, this solution is this example is not achieved within each PDAC/NDAC pair. Instead, it is achieved by effectively combining all of the PDACs 1-4 in PDAC section 172p together to form one large PDAC, and all of the NDACs 1-4 in NDAC section 172n together to form one large NDAC. This way, optimal performance can be achieved while keeping the size of each of the individual PDACs 1-4 and NDACs 1-4 reasonable.

As shown in FIG. 10A, the stimulation circuitry 170 includes a high resolution current register 169, which can send a control signal X to each of the PDCs 1-4 to inform whether the high resolution current mode has been entered. When X is asserted, X=1, the PDCs 1-4 are informed that PDACs 1-4 and NDACs 1-4 are to be used together to form a single timing channel. In other words, in the high resolution current mode, only one group of pulses can be formed at the electrodes 16 (compare FIG. 6). When X is not asserted, the stimulation circuitry 170 runs in the standard current mode, as described previously, with each PDC controlling its PDAC/NDAC pair to form pulses in a timing channel.

As shown in FIG. 10A, operation in the high resolution current mode modifies the control signals issued by the PDCs 1-4 so that in some instances they carry the same signals. For example, each PDC issues the same control signals <J> to its PDAC/NDAC pair so that the master DACs 185 in each PDAC and each NDAC is set to the same value. Operation in the high resolution current mode also affects the K control signals, which are each asserted, K=1, and sent to each PDAC and each NDAC to set the resistance of the resistance block 187 in each.

The switch matrix control signals <C> remain unaffected in so far as each PDC 1-4 sends unique control signals to each PDAC 1-4 and NDAC 1-4. This is still required to ensure that appropriate branches in each of the DACs can still be connected to the correct electrode nodes 61a. However, these control signals <C> are issued in a cooperative fashion to form pulses in the single timing channel that the high resolution current mode enables, as discussed further below.

(In the high resolution current mode, resistor control signals <R> (see FIGS. 5A and 8) used to tune variable reference resistor Rc in each of the PDACs 1-4 and NDACs 1-4 to produce reference voltage Vref=100 mV can remain specific to each PDAC and each NDAC as in FIG. 5A, or can remain specific to each PDAC/NDAC pair as in FIG. 8, or could comprise a single set of control signals issued to all of the PDACs and NDACs. These control signals <R> are not shown in FIG. 10A for simplicity).

FIG. 10B shows functionally how the combined NDACs 1-4 would operate in the high resolution current mode. Particular focus is shown as regards the switch matrices 190(1) to 190(4) in each of the NDACs 1-4, which are individually shown. The other circuitry shown in FIG. 10B would also be repeated in each of the NDACs, but this is not shown for simplicity.

In effect, operation in the high resolution current mode drops the current Ib formed in each branch, but increases the numbers of branches. The current in each branch is reduced because K is asserted, K=1. As explained earlier (FIG. 5F), this reduces the current Ib in each branch by a factor of 1/M (e.g., ¼), where M equals the number of asserted resistance transistors 188 in the resistance blocks 187. The increased number of branches (e.g., to Lmax=100) results from combined effect of each of the switch matrices 190(1)-(4). As shown, and by virtue of operation in the high resolution current mode, PDC1 issues switch matrix control signals $C_{1,X}$ to $C_{25,X}$, allowing any of branch transistors 184(1)-(25) to provide current to electrode node X; PDC2 issues control signals $C_{26,X}$ to $C_{50,X}$; PDC3 issues control signals $C_{51,X}$ to $C_{75,X}$; and PDC4 issues control signals $C_{76,X}$ to $C_{100,X}$. Functionally, the combined PDACs would look similar, but this isn't shown for simplicity.

Notice given the example in FIG. 10B that the decrease in branch current (×¼) is offset by the effective increase in the number of branches (×4), meaning that the combined NDAC can produce a maximum current, Imax=−25.5 mA (at J=Jmax=255 and L=Lmax=100)), which maximum current is equal to operation of any of the NDACs individually when operating in the standard current mode (when K=0). This assures a timing channel that produces a reasonably safe amount of current, and with a higher resolution, as discussed next.

FIG. 10C revisits the example of FIGS. 9A and 9B, in which current is moved from cathode electrode E2 to E3, but in operation in the high resolution current mode. When high resolution current register 169 asserts high resolution current mode control signal X ('1'), each of the PDCs 1-4 automatically asserts K=1 to their PDAC/NDAC pairs. J is then set to a value that will produce values for +I and −I in the combined PDAC and combined NDAC that match the total source and sink currents needed: +10 mA and −10 mA in this example. Because K='1', a value of J=100 will produce I=+/−10 mA in the combined PDAC/NDAC if all Lmax=100 branches in these DACs are asserted.

The source current of the combined PDAC isn't being moved between anode electrodes in this example, and will remain at E1. Thus, the entirety of the source current I=+10 mA is sent to anode electrode E1, which occurs by asserting all of switch matrix control signals $C_{1,1}$ to $C_{1,100}$. Notice that this takes coordination between the PDCs 1-4, each of which is responsible for issuing one quarter (<Cp1>, <Cp2>, <Cp3>, and <Cp4>) of these switch matrix control signals. In other words, all 100 branches in the combined PDAC will send their currents to anode electrode E1, which sums to +10 mA as desired.

At time t=0, the entirety of the sink current at the combined NDAC, I=−10 mA, is sent to cathode electrode E2, which occurs by asserting all of switch matrix control signals $C_{2,1}$ to $C_{2,100}$. Again, this takes coordination between the PDCs 1-4, each of which is responsible for issuing one quarter (<Cn1>, <Cn2>, <Cn3>, and <Cn4>) of these switch matrix control signals. In other words, all 100 branches in the combined NDAC will send their currents to electrode E2, which sums to −10 mA as desired. None of the branches are connected to electrode E3 at this time.

At time t=1, a small amount of current has been moved from E2 to E3 (−0.1 mA), which occurs by connecting one of the branches to E3 ($C_{3,100}$), one of the control signals in <Cn4> issued by PDC4. As this branch (see branch transistor 184(100) in FIG. 10B) can no longer be connected to E2, E2 only receives −9.9 mA ($C_{2,1}$ to $C_{2,99}$). (Notice that the resolution is higher compared to FIG. 9B—from −0.4 mA to −0.1 mA, or from 4% to 1% (I/Lmax)).

This process continues, with additional branches being connected one at a time to E3 (more of $C_{3,x}$ are asserted, while less of $C_{2,x}$ are asserted), moving another increment of −0.1 mA each time. Although not shown, at time t=25, <Cn1>, <Cn2> and <Cn3> from PDCs 1-3 will be asserted to connect branch transistors 184(1)-(75) to E2 ($C_{2,1}$ to $C_{2,75}$); <Cn4> from PDC4 will be asserted to connect branch transistors 184(76)-(100) to E3 ($C_{3,76}$ to $C_{3,100}$). And at time t=50, <Cn1> and <Cn2> from PDC1 and PDC2 will be asserted to connect branch transistors 184(1)-(50) to E2 ($C_{2,1}$ to $C_{2,50}$); <Cn4> and <Cn3> from PDC3 and PDC4 will be asserted to connect branch transistors 184(51)-(100) to E3 ($C_{3,51}$ to $C_{3,100}$); etc., showing cooperation between the PDCs and their PDAC/NDAC pairs to produce pulses in a single timing channel with the proper amplitude at the selected electrodes.

Eventually, at time t=100, it is seen that all of the branches in the combined NDAC are connected to cathode electrode E3 ($C_{3,1}$ to $C_{3,100}$) and no branches are connected to E2. Thus cathode E3 receives all of the sink current (−10 mA), and cathode E2 receives none. In short, the entirety of the sink current has been moved in −0.1 mA increments from E2 to E3. Further, because the currents in the combined PDAC/combined NDAC have been set to +I/−I, and all Lmax=100 branches are always asserted in each, the total source current and total sink current is balanced, even though −I is shared between cathode electrodes E2 and E3 in different proportions at different times.

Figure 11:
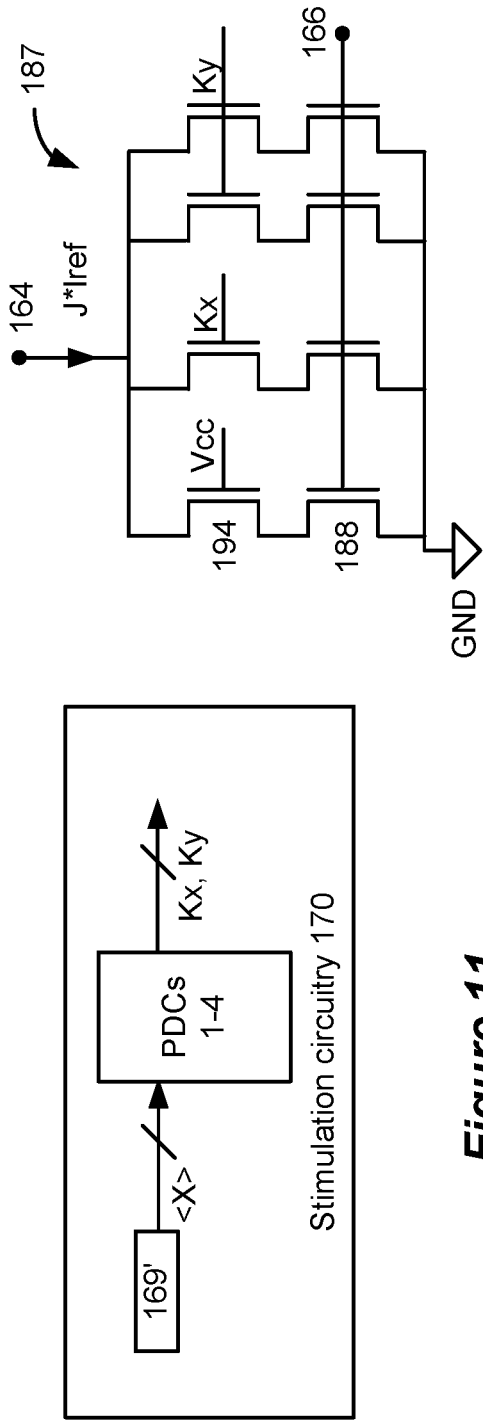
FIG. 11 shows modification to the improved DAC circuitry to include the use of standard, medium, and high resolution modes, each forming mode forming different numbers of timing channels, in accordance with an example the invention.

Other modifications to the DAC circuitry 172 are possible. For example, as described to this point, the resistance block 187 (FIGS. 5B, 5D) includes resistance transistors 188 controlled by a single control signal (e.g., Kn1), thus allowing the resistance of the resistor block 187 to be changed to two values, which allows the branch currents Ib to be changed to two values. However, further levels of resistance (more than two) could be produced by the resistance block 187, as shown in FIG. 11. FIG. 11 shows resolution register 169', which issues a plurality of control signals <X> to the PDCs. These control signals <X> inform whether the PDCs are to operate in standard, medium, or high resolution current modes. Depending on the mode chosen, the PDCs can cooperate to issue appropriate control signals Kx and Ky to the resistance blocks in their associated PDAC/NDAC pair, and further cooperate so as to control their PDAC/NDAC in a combined fashion with other PDACs/NDACs to form differing numbers of timing channels with differing current resolutions.

In one example, in the standard mode, Kx=Ky=0, and thus only one resistance transistor 188 is selected. This is as described earlier (e.g., FIG. 5E), in which the branch currents Ib1 are relatively high, but where each of the PDAC/NDAC pairs operates to form pulses in its own timing channel. Thus, there are four timing channels TC1-TC4, and a lower current resolution of 4% (assuming Lmax=25). In the high mode, Kx=Ky=1, and thus all (M=4) resistance transistors are selected. This is also as described earlier (e.g., FIG. 5F), in which the branch currents Ib3 are relatively low (Ib1=4*Ib3), and where all of the PDACs and all of the NDACs are combined to form pulses in a single timing channel (FIGS. 10A-10C) with a high resolution (1%).

In a medium mode, Kx=1, and Ky=0. This would include only two resistance transistors 188 in the resistance block 187, and it should be clear from the foregoing description that the branch currents Ib2 formed in each PDAC and NDAC in this instance would intermediate (Ib1=2*Ib2=4*Ib3). In this circumstance, it may be desired to combine only some of the PDACs (e.g., PDAC1+PDAC 2, and PDAC3+PDAC4) and some of the NDACs (e.g., NDAC1+NDAC 2, and NDAC3+NDAC4), thus forming two timing channels for stimulation pulses. It should be clear from the foregoing that the combined PDACs and NDACs in this instance would have 50 branch transistors (Lmax=50), and a medium resolution of 2%. Further, because the number of branch currents (Lmax) in each timing channel scales in inverse proportion to the branch currents Ibx, the maximum current providable by each timing channel stays constant at a desired safe value (+/− 25.5 mA).

Figure 12:
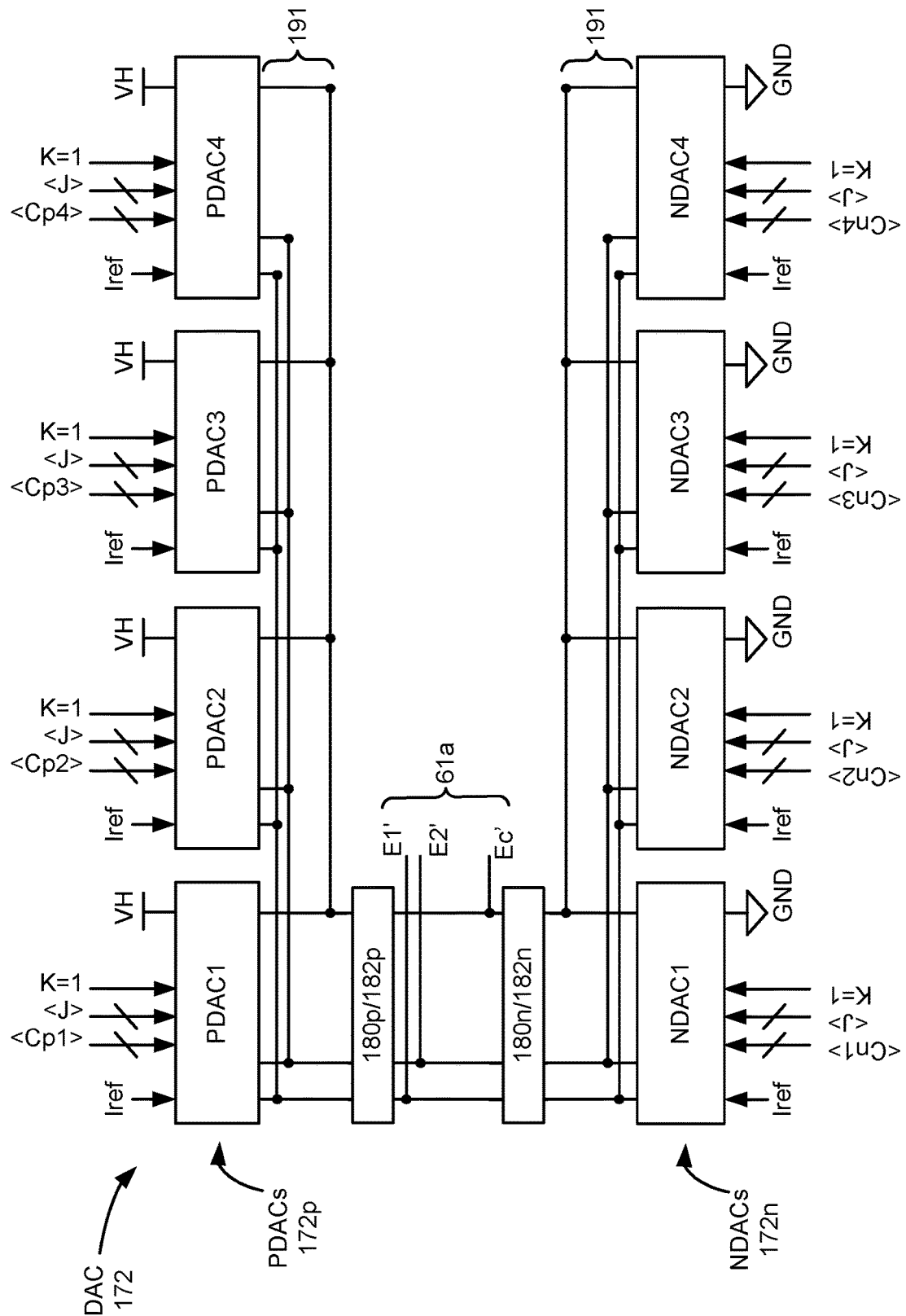
FIG. 12 shows alternative circuitry for the improved DAC circuitry in which a first output stage is shared by the NDACs and a second output stage is shared by the PDACs, in accordance with an example of the invention.

An alternative architecture for the DAC circuitry 172 is shown in FIG. 12. In this example, the output stages—the op amps 180 and output transistors 182—are moved from each of the PDACs and the NDACs, and instead a single output stage 180p/182p is shared between each of the PDACs, and a single output stage 180n/182n is shared between each of the NDACs. Each of the switch matrix outputs 191 from the each of the PDACs are sent to output stage 180p/182p for connection to the electrode nodes 61a, and each of the switch matrix outputs 191 from the each of the NDACs are sent to output stage 180n/182n for connection to the electrode nodes 61a. This architecture can save space on the ASIC 160, particular because of reduction in the total number of output transistors 182. As explained further below, the output transistors are high-voltage transistors, and thus are relative large.

Although not shown, in FIG. 12, remember that both inputs to the op amps 180 are held at Vref (FIG. 5B) in the NDACs, and VH-Vref in the PDACs (FIG. 7). Thus, these reference voltages can be sent from the NDAC or PDAC whose currents the output stages 180n/182n or 180p/182p are currently passing to the electrode nodes 61a. That is, the output stages 180n/182n or 180p/182p can select Vref or VH-Vref from the appropriate NDAC or PDAC. Alternatively, a single Vref may be produced to service all NDACs and their output stage 180n/182n, and a single Vref may be produced to service all PDACs and their output stage 180p/182p.

As noted earlier, the PDACs 1-4 and NDACs 1-4 include additional power supply voltages, as shown in FIG. 13A.

Specifically, each PDACx includes a higher power supply voltage comprising the compliance voltage VH and a lower power supply voltage Vssh. Each NDACx includes a higher power supply voltage Vcc and a lower power supply voltage of ground (GND; 0V). Because VH/Vssh are higher than Vcc/ground, VH/Vssh is referred to as a high power domain, and Vcc/ground is referred to as a low power domain. Connection of certain circuity in the NDACs to its power supply voltages Vcc and ground can be seen in FIG. 5B. Likewise, connection of certain circuitry in the PDACs to its power supply voltages VH and Vssh can be seen in FIG. 7.

The reason the PDACs are powered in the high power domain while the NDACs are powered in the low power domain relates to the fact that the compliance voltage VH connected to the PDACs can be large, and can vary. Variation of the compliance voltage VH was explained briefly in the Background, and is elaborated upon further with respect to FIG. 13A. The voltage drop across the patient tissue, Rt, may not be known or may change over time, and hence the voltage dropped across the tissue in response to a stimulation current I (Vrt=I*Rt) may also change. Measuring the voltage drops across the active PDACs (Vp) and the active NDAC circuit (Vn) can assist in determining the tissue's voltage drop and resistance, and hence whether compliance voltage VH should be increased or decreased. Thus, in FIG. 13A, it is seen that the compliance voltage generator block 76 (FIG. 4B) that produces the compliance voltage VH receives the measured PDAC and NDAC voltages drops Vp and Vn, and adjusts compliance voltage VH accordingly. In actuality, the measured voltage drops may be measured at sample and hold circuitry 68 (FIG. 4B) as described earlier, and then presented to the compliance voltage generator block 76 to allow for compliance voltage VH adjustment, but this intermediate detail is not shown in FIG. 13A.

The relevant point is that the compliance voltage VH can change over time. Further, the compliance voltage VH may be set to voltages that are relatively large, such as from 6 to 15 Volts. Higher voltage requirements have generally required PDACs and NDACs to be formed of special high-voltage transistors. Such high-voltage transistors are generally larger and more complicated to fabricate compared to more-standard, smaller logic transistors, because they are designed to function when receiving high voltages at their gates (i.e., Vg=0 to VH), and when receiving high voltages across their drains and sources (i.e. Vds=0 to VH). Even if the compliance voltage is normally not required to operate at its maximum voltage (e.g., 15V), the PDAC and NDAC transistors have traditionally been built to withstand the possibility of high voltages, which complicates PDAC and NDAC design on the ASIC.

The inventors realize that it is beneficial to provide different power supply domains in the PDACs and NDACs of the DAC circuitry 172, because this can enable most of the transistors in the PDACs and NDACs to be made from more-standard, smaller logic transistors otherwise used to form logic gates in the ASIC 160. Thus, as already discussed, the PDACs operate in a high power domain comprising VH and Vssh, while the NDACs operate in a low power domain comprising Vcc and ground. In one example, Vssh is always 3.3 Volts lower than VH in the high power domain, and so both the higher power supply VH and lower power supply Vssh for the PDACs are variable. In another example, Vcc is always 3.3 Volts higher than ground, and so neither the higher power supply Vcc nor the lower power supply ground for the NDACs is variable.

The control signals sent to the PDACs and NDACs (e.g., <C>, <J>, K, and <R>) are also referenced to the appropriate power domain. Thus, the voltages of the logic states sent to the PDACs are set to VH (a logic '1', denoted as '1p' in the figures) and Vssh (a logic '0', denoted as '0p'). The PDAC control signal voltages can vary as VH varies. The voltages of the logic states sent to the NDACs are set to Vcc (a logic '1', denoted as '1n') and ground (a logic '0', denoted as '0n'). These NDAC control signals voltages are preferably not variable. The transistors used to build the PDACs and NDACs are also biased to their appropriate power domain, as discussed subsequently.

FIG. 13B shows generator circuitry 202, 204 used respectively to generate voltage Vssh for the PDACs and Vcc for the NDACs. Both of these generators 202, 204 comprise linear voltage regulators and include an op amp 206 that controls a pass transistor 210. Vssh generator 202 is described first. A reference resistor Rp (e.g., 3.3 Megaohm) is connected between the compliance voltage VH and one of the op amp 206's inputs. A reference current source 208 pulls a current of one microamp through the reference resistor Rp, thus dropping a reference voltage Vrp equal to 3.3 V across the reference transistor. This presents a voltage of VH—3.3V to the input of the op amp 206. Feedback through pass transistor 210 forces the other input of the op amp 206—the output Vssh of the generator 202—to the input voltage, and thus an output voltage of Vssh=VH-3.3 V is produced. Note that even though VH may vary as described earlier, the output of generator 202 is always (in this example) 3.3 V lower than VH, as set by the resistor Rp and current source 208. A voltage other than 3.3 V could also be used, and Vssh 202 generator can be designed in different manners.

Vcc generator 204 used to produce the Vcc power supply voltage for the NDACs can be similar in structure to the Vssh generator 202. A reference resistor Rn and current source 208 drawing from the battery voltage Vbat can be used to form a reference voltage Vrn of 3.3 V, which is input to the op amp 206. Feedback will again force the other input of the op amp 206—the output Vcc of the generator 204—to Vcc=Vrn=3.3 V. The Vcc generator 204 in this example is thus not variable. It should be noted that Vcc may also be used to power other circuitry in the IPG 10, such as various functional blocks included in the ASIC 160 (FIG. 4B). Again, a voltage other than 3.3 V could also be used, and Vcc generator 204 can be designed in different manners. The various generators 202 and 204, including the VH generator 76, may also be formed of a single circuit, although in this instance they can still be referred to as discrete generator circuits.

Figure 14A:
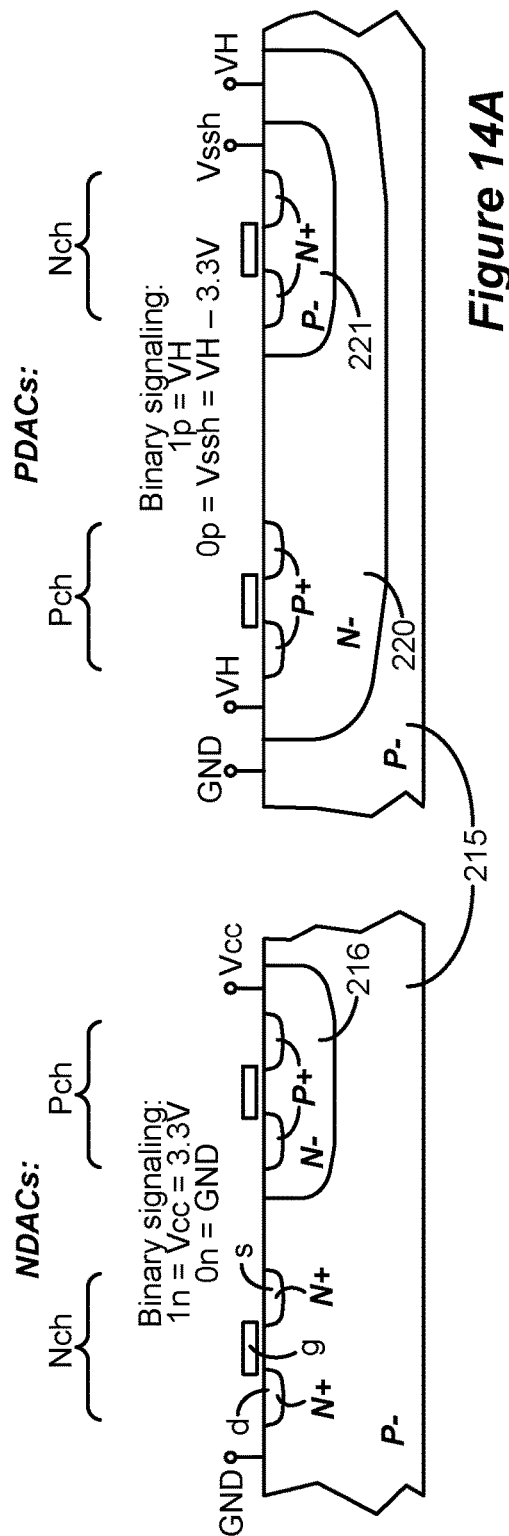
FIG. 14A shows cross sections of the N- and P-channel transistors in both the NDACs and the PDACs, and shows how they are respectively biased in the low and high power domains, in accordance with an example of the invention.

As noted earlier, the low-voltage transistors used to build the NDACs and PDACs are preferably biased in accordance with their appropriate power domain. This is shown in FIG. 14A, which shows cross-sectional views of the monolithic substrate 215 of the ASIC 160. Both the NDACs and the PDACs include both low-voltage N-channel (Nch) and low-voltage P-channel (Pch) transistors. For example, and referring to FIGS. 5B-5D, the NDACs include N-channel transistors 194, 188, 184, and 178 described earlier, as well as N-channel transistors inherent in the op amps 168 and 180. The NDACs also include P-channel transistors 173, 174, 186, and 192 described earlier, as well as P-channel transistors inherent in the op amps 168 and 180. The polarity of these transistors are inverted in the PDACs, as shown in FIG. 7. Thus, the PDACs include P-channel transistors 194, 188, 184, 178, and within the op amps 168 and 180. The PDACs also include N-channel transistors 173, 174, 186, 192, and within the op amps 168 and 180.

As FIG. 14A shows, the NDAC transistors are essentially formed as is common in CMOS technologies, with the N-channel transistors built into a grounded P-type substrate 215, and the P-channel transistors built in an N-well 216 biased to Vcc=3.3 V. In other words, the NDAC transistors are biased to the Vcc/ground low power domain.

The PDAC transistors are biased to the VH/Vssh high power domain. Thus, a high-voltage N-well 220 is formed in the P-type substrate 215, and biased to the compliance voltage VH. This high voltage N-well 220 may be deeper and significantly graded so that it may retain the high compliance voltage VH (which may be up to 15 Volts) without breaking down to the grounded substrate 215. P-channel transistors are built in the high-voltage N-well 220. A P-well 221 is formed in the N-well 220, in which the N-channel transistors may be built. The P-well 221 is biased to Vssh, and so the PDAC transistors are biased to the VH/Vssh high power domain.

The only high-voltage transistors required in the design of DAC circuity 172 are the output transistors 182 (FIGS. 5B, 7) used to pass currents to the selected electrode nodes 61a. (The outputs of op amps 180 may also be translated to appropriately operate the gates of these transistors 182).

Figure 14B:
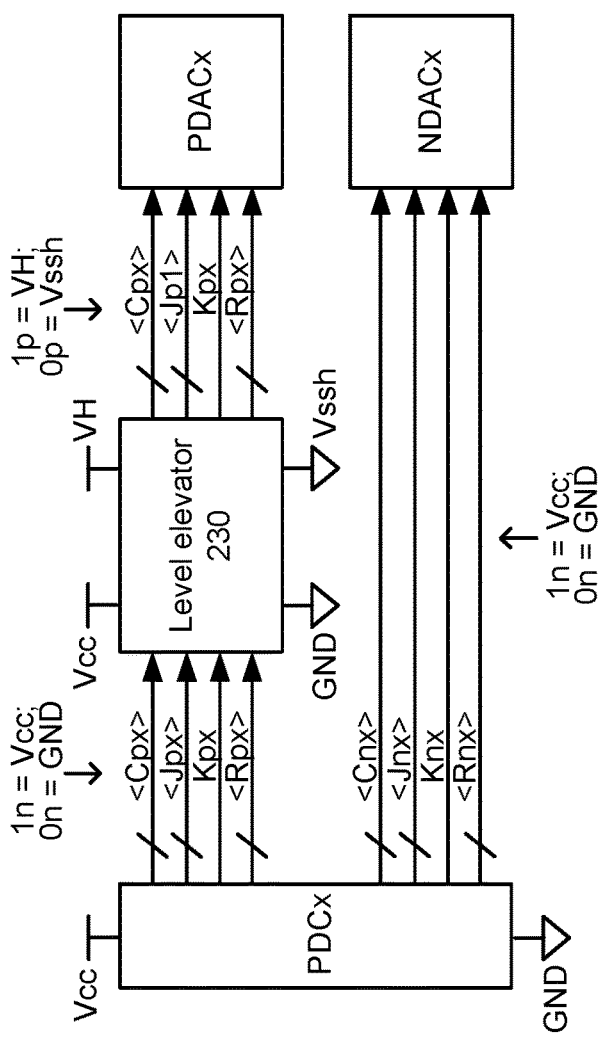
FIG. 14B shows how control signals sent to the PDACs can be level elevated from the low power domain to the high power domain.

The control signals sent to the PDACs and NDACs (e.g., <C>, <J>, K, and <R>) are also referenced to the appropriate power domain. These control signals as discussed earlier are issued from the pulse definition circuits (PDCs). As shown in FIG. 14B, because the PDCs are powered by Vcc and ground, the NDAC control signals (<Cnx>, <Jnx>, Knx, and <Rnx>) and the PDAC control signals (<Cpx>, <Jpx>, Kpx, and <Rpx>) are issued with logic states equaling those values (0n=ground; 1n=Vcc). In other words, the PDCs operate in the same Vcc/ground low power domain as the NDACs. Therefore, the NDACs can receive its control signals directly from the PDCs without conversion as shown. Because the voltages of the logic states of these control signals equal the voltages to which the N-channel and P-channels are biased (FIG. 14A), voltage drops in the NDACs' transistors will not exceed Vcc=3.3 Volts, and thus low-voltage transistors can be used in the NDACs.

The PDACs however operate in the VH/Vssh high power domain, which may be significantly higher than the Vcc/ground low power domain at which its control signals are issued by the PDCs. Therefore, each control signals destined for the PDACs is sent to a level elevator 230 to increases the voltage of the signal, as shown in FIG. 14B. Circuitry for the level elevator 230 is shown in detail in FIG. 14C, and includes a low power domain stage 232 which like the PDCs and the NDACs is powered by Vcc and ground, and a high power domain stage 234 which like the PDACs is powered by VH and Vssh. The low domain stage 232 receives a particular control signal (Dn) at its input which varies from 0n=ground to 1n=Vcc. Inverters 236 buffer this input, and reproduce Dn and its complement Dn*.

Dn and Dn* are each presented to a capacitor 238, which removes any DC bias from the signals, and then presents them to inputs of a cross-coupled latch circuit 244 powered by VH and Vssh in the high power domain stage 234. As one skilled will appreciate, the cross coupling in the latch circuit 244 will detect the difference between Dn and Dn*, and produce corresponding outputs Dp and Dp* pulled to VH or Vssh. Further buffering by inverters 246 then produces an output Dp which is equivalent to Dn, but varying from 0p=Vssh to 1p=VH in the high power domain. The level-elevated control signal can now be sent to its appropriate PDAC. (Note that the level elevator 230 also produces the complement of Dp, Dp*, which may also be sent to the PDAC if an inverted version of the control signal is more useful). Again, because the voltages of the logic states of these control signals equal the voltages to which the N-channel and P-channels are biased (FIG. 14A), voltage drops in the PDACs' transistors will not exceed 3.3 Volts (VH-Vssh), and thus low-voltage transistors can be used in the PDACs.

(Transistors 240 and 242 receiving signals clear (clr) and preset (pst) are useful upon initial powering of the ASIC 160 because the latches 244 in the level elevators 230 may power to an indefinite state that is inconsistent with the input, Dn. Thus, one of these signals dr or pst can be asserted after power-up to pre-condition the latch 244 to match the current input value Dn. For example, if Dn=0n, dr can be asserted; if Dn=1n, pst can be asserted).

Note that the PDACs can use low-voltage transistors even though the compliance voltage VH may change over time. If VH changes, so too will Vssh, as dictated by the operation of the Vssh generator 202 (FIG. 13B), which always maintains a 3.3 V difference between Vh and Vssh in the high power domain, which happens in the examples shown to equal the same 3.3 V difference between Vcc and ground in the low power domain. If VH and Vssh change, so will the biasing of the transistors in the PDACs (FIG. 14A), and so too will the voltages of the logic states presented to those transistors (per operation of the level elevators of FIG. 14C). This is shown in FIG. 14D, which shows that as the compliance voltage VH varies over time, so too does Vssh, and so do the voltages of the logic states 0p, 1p produced by the level elevators 230. Moreover, the 3.3 V difference is also maintained. FIG. 14D also shows the power supplies for the NDACs (Vcc, ground) and the voltages of the logic states in this low power domain (0n, 0p), which also maintain a 3.3 V difference. Although constant, the low power domain could also be made to vary.

While disclosed in the context of an implantable pulse generator, it should be noted that the improved stimulation circuitry 170 and DAC circuitry 172 could also be implemented in a non-implantable pulse generator, such as an External Trial Stimulator (ETS). See, e.g., U.S. Pat. No. 9,259,574 (describing an ETS).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:
1. A pulse generator, comprising:
a plurality of electrode nodes, each electrode node configured to be coupled to an electrode to provide stimulation pulses to a patient's tissue; and
digital-to-analog converter circuitry, comprising
a source circuit configured to source a source current to any of the electrode nodes, wherein the source circuit is powered by a first power supply voltage and a second power supply voltage defining a first power domain, and
a sink circuit configured to sink a sink current from any of the electrode nodes, wherein the sink circuit is powered by a third power supply voltage and a fourth power supply voltage defining a second power domain, where the first, second, third, and fourth power supply voltage are different from each other.

2. The pulse generator of claim 1, further comprising at least one first control signal received by the source circuit to control the source current sourced to any of the electrode nodes, wherein the at least one first control signal comprises logic signals with voltages of the first power domain.

3. The pulse generator of claim 1, further comprising control circuitry configured to issue at least one preliminary control signal comprising logic signals with voltages of the second power domain, and further comprising at least one level elevator, wherein each level elevator changes the voltages of one of the at least one preliminary control signals from the second power domain to the first power domain to form one of the at least one first control signals.

4. The pulse generator of claim 3, wherein the control circuitry is further configured to issue at least one second control signal received by the sink circuit to control the sink current sunk from any of the electrode nodes, wherein the at least one second control signal comprises logic signals with voltages of the second power domain.

5. The pulse generator of claim 1, wherein the first and second power supply voltages defining the first power domain are configured to vary.

6. The pulse generator of claim 5, wherein the variable second power supply voltage comprises a fixed difference with the variable a first power supply voltage.

7. The pulse generator of claim 5, wherein the first and second power supply voltages are configured to vary based on a first measurement taken from the source circuit and/or a second measurement taken from the sink circuit.

8. The pulse generator of claim 5, wherein the third and fourth power supply voltages defining the second power domain are constant.

9. The pulse generator of claim 1, wherein the source circuit comprises P-type and N-type transistors biased to the first or second power supply voltages, and wherein the sink circuit comprises P-type and N-type transistors biased to the third or fourth power supply voltages.

10. The pulse generator of claim 1, wherein the first and second power supplies differ by a first voltage magnitude, and the third and fourth power supplies differ by the first voltage magnitude.

11. The pulse generator of claim 1, further comprising at least one implantable lead, wherein the electrodes are located on the lead.

12. A pulse generator, comprising:
a plurality of electrode nodes, each electrode node configured to be coupled to an electrode to provide stimulation pulses to a patient's tissue;
a first digital-to-analog converter configured to provide a first current to any of the plurality of electrode nodes, wherein the first digital-to-analog converter is powered by a first power supply voltage and a second power supply voltage defining a first power domain;
a first generator configured to produce the first power supply voltage, wherein the first generator is configured to vary the first power supply voltage based at least on a first measurement taken from the first digital-to-analog converter; and
a second generator configured to produce the second power supply voltage with a fixed difference with the varying first power supply voltage.

13. The pulse generator of claim 12, further comprising:
a second digital-to-analog converter configured to provide a second current to any of the plurality of electrode nodes, wherein the second digital-to-analog converter is powered by a third power supply voltage and a fourth power supply voltage defining a second power domain; and
a third generator configured to produce the third power supply voltage, wherein the third generator is configured to produce the third power supply voltage with a fixed difference to the fourth power supply voltage.

14. The pulse generator of claim 13, wherein the first digital-to-analog converter sources the first current to any of the plurality of electrode nodes, and wherein the second digital-to-analog converter sinks the second current from any of the plurality of electrode nodes.

15. The pulse generator of claim 14, wherein the first digital-to-analog converter is controlled by at least one first control signal comprising logic signals with voltages of the first power domain, and wherein the second digital-to-analog converter is controlled by at least one second control signal comprising logic signals with voltages of the second power domain.

16. The pulse generator of claim 13, wherein the third and fourth power supply voltages defining the second power domain are constant.

17. The pulse generator of claim 16, wherein the third power supply voltage comprise a fixed difference with the fourth power supply voltage that equals the fixed difference between the first and second power supply voltages.

18. The pulse generator of claim 12, further comprising a battery with a battery voltage, wherein the first generator comprises boost circuitry configured to produce the first power supply voltage from the battery voltage.

19. The pulse generator of claim 12, wherein the first digital-to-analog converter is controlled by at least one first control signal comprising logic signals with voltages of the first power domain.

20. The pulse generator of claim 19, further comprising control circuitry configured to issue at least one preliminary control signal, and further comprising at least one level elevator, wherein each level elevator changes one of the at least one preliminary control signals to form one of the at least one first control signals.

21. The pulse generator of claim 12, wherein the first power supply voltage is higher than the second power supply voltage, and wherein the first digital-to-analog converter comprises P-type transistors biased to the first power supply voltage, and N-type transistors biased to the second power supply voltage.

22. The pulse generator of claim 12, further comprising at least one implantable lead, wherein the electrodes are located on the lead.

* * * * *